(12) United States Patent
Arnold et al.

(10) Patent No.: US 11,626,031 B2
(45) Date of Patent: Apr. 11, 2023

(54) SYSTEMS AND TECHNIQUES FOR TRACKING SLEEP CONSISTENCY AND SLEEP GOALS

(71) Applicant: Fitbit, Inc., San Francisco, CA (US)

(72) Inventors: Jacob Antony Arnold, Fremont, CA (US); Yeqing Cheng, San Carlos, CA (US); Yasaman Baiani, San Francisco, CA (US); Allison Maya Russell, Berkeley, CA (US)

(73) Assignee: FITBIT, INC., San Francisco, CA (US)

( * ) Notice: Subject to any disclaimer, the term of this patent is extended or adjusted under 35 U.S.C. 154(b) by 685 days.

(21) Appl. No.: 16/442,304

(22) Filed: Jun. 14, 2019

(65) Prior Publication Data

US 2019/0371197 A1 Dec. 5, 2019

Related U.S. Application Data

(63) Continuation of application No. 15/171,049, filed on Jun. 2, 2016, now Pat. No. 10,325,514.

(51) Int. Cl.
*G09B 19/00* (2006.01)
*G09B 5/00* (2006.01)
(Continued)

(52) U.S. Cl.
CPC .............. *G09B 19/00* (2013.01); *A61B 5/486* (2013.01); *A61B 5/4809* (2013.01);
(Continued)

(58) Field of Classification Search
CPC ..... A61B 5/4809; A61B 5/4815; A61B 5/486; A61B 5/7405; A61B 5/742; A61B 5/743;
(Continued)

(56) References Cited

U.S. PATENT DOCUMENTS

| 4,836,219 A | 6/1989 | Hobson et al. |
| 5,724,990 A | 3/1998 | Ogino |

(Continued)

FOREIGN PATENT DOCUMENTS

| CN | 103717125 | 4/2014 |
| CN | 103919536 | 7/2014 |

(Continued)

OTHER PUBLICATIONS

U.S. Final Office Action, dated Oct. 11, 2019, issued in U.S. Appl. No. 15/438,643.

(Continued)

*Primary Examiner* — Jack Yip
(74) *Attorney, Agent, or Firm* — Dority & Manning, P.A.

(57) ABSTRACT

Methods, techniques, apparatuses, and systems for setting up and tracking sleep consistency goals of users are provided. In one example, a computing system for setting a sleep schedule of a user of a biometric monitoring device may obtain sleep data derived from sensor data generated by the biometric monitoring device, store the sleep data in a sleep log data store as one or more sleep logs associated with an account assigned to the user, and calculate a target bedtime based on a scheduled waketime of the user and a sleep efficiency derived, at least in part, from the sleep data for one or more users stored in the sleep log data store. The computing system may also be configured to provide a number of personalized user interfaces to an individual for the purposes of setting a sleep schedule. Such interfaces may include parameters that are tailored to the individual sleep needs and/or characteristics of the individual's sleep.

28 Claims, 15 Drawing Sheets

(51) Int. Cl.
| | | |
|---|---|---|
| *G06F 3/0484* | (2022.01) | |
| *A61B 5/00* | (2006.01) | |
| *G06F 3/0481* | (2022.01) | |
| *G06F 3/04842* | (2022.01) | |
| *A61B 5/11* | (2006.01) | |

(52) U.S. Cl.
CPC ............ *A61B 5/4815* (2013.01); *A61B 5/742* (2013.01); *A61B 5/743* (2013.01); *A61B 5/7405* (2013.01); *A61B 5/7455* (2013.01); *A61B 5/7475* (2013.01); *G06F 3/0481* (2013.01); *G06F 3/0484* (2013.01); *G06F 3/04842* (2013.01); *G09B 5/00* (2013.01); *A61B 5/1118* (2013.01); *A61B 5/4806* (2013.01); *A61B 5/4812* (2013.01)

(58) Field of Classification Search
CPC ... A61B 5/7455; A61B 5/7475; A61B 5/1118; A61B 5/4806; A61B 5/4812; G09B 19/00; G09B 5/00; G06F 3/0481; G06F 3/0484; G06F 3/04842
See application file for complete search history.

(56) References Cited

U.S. PATENT DOCUMENTS

| | | | |
|---|---|---|---|
| 5,902,250 | A | 5/1999 | Verrier et al. |
| 6,964,641 | B2 | 11/2005 | Cho et al. |
| 7,306,567 | B2 | 12/2007 | Loree, IV |
| 7,578,793 | B2 | 8/2009 | Tadros et al. |
| 7,674,230 | B2 | 3/2010 | Reisfeld |
| 8,002,553 | B2 | 8/2011 | Hatlestad et al. |
| 8,273,035 | B2 | 9/2012 | Russo et al. |
| 8,292,819 | B2 | 10/2012 | Kuo et al. |
| 8,548,770 | B2 | 10/2013 | Yuen et al. |
| 8,606,356 | B2 | 12/2013 | Lee et al. |
| 8,684,900 | B2 | 4/2014 | Tran |
| 8,690,751 | B2 | 4/2014 | Auphan |
| 8,712,723 | B1 | 4/2014 | Kahn et al. |
| 8,764,651 | B2 | 7/2014 | Tran |
| 8,793,522 | B2 | 7/2014 | Rahman et al. |
| 8,812,259 | B2 | 8/2014 | Messenger et al. |
| 8,942,779 | B2 | 1/2015 | Halperin et al. |
| 9,675,281 | B2 | 6/2017 | Arnold et al. |
| 9,808,185 | B2 | 11/2017 | Arnold et al. |
| 9,820,680 | B2 | 11/2017 | Muzet |
| 10,092,219 | B2 | 10/2018 | Arnold et al. |
| 10,311,745 | B2 | 6/2019 | Arnold et al. |
| 10,325,514 | B2 | 6/2019 | Arnold et al. |
| 2002/0017994 | A1* | 2/2002 | Balkin ................ A61B 5/4806 340/573.1 |
| 2004/0087878 | A1 | 5/2004 | Krausman et al. |
| 2005/0043652 | A1 | 2/2005 | Lovett et al. |
| 2005/0113650 | A1 | 5/2005 | Pacione et al. |
| 2005/0119711 | A1* | 6/2005 | Cho ................... A61B 5/4818 607/42 |
| 2005/0209511 | A1 | 9/2005 | Heruth et al. |
| 2005/0209512 | A1 | 9/2005 | Heruth et al. |
| 2006/0019224 | A1* | 1/2006 | Behar ................ A61B 5/4809 434/236 |
| 2006/0020177 | A1 | 1/2006 | Seo et al. |
| 2006/0031102 | A1 | 2/2006 | Teller et al. |
| 2006/0200008 | A1* | 9/2006 | Moore-Ede ............ B60K 28/06 128/920 |
| 2006/0224051 | A1 | 10/2006 | Teller et al. |
| 2006/0241359 | A1 | 10/2006 | Nagai et al. |
| 2006/0281978 | A1 | 12/2006 | Crucilla |
| 2007/0161873 | A1 | 7/2007 | Ni et al. |
| 2007/0191742 | A1 | 8/2007 | Park |
| 2007/0208233 | A1 | 9/2007 | Kovacs |
| 2008/0287751 | A1 | 11/2008 | Stivoric et al. |
| 2008/0306351 | A1 | 12/2008 | Izumi |
| 2009/0164219 | A1 | 6/2009 | Yeung et al. |
| 2010/0056907 | A1 | 3/2010 | Rappaport et al. |
| 2010/0099954 | A1* | 4/2010 | Dickinson ............. G09B 19/00 600/300 |
| 2010/0102130 | A1 | 4/2010 | Madej et al. |
| 2010/0295684 | A1 | 11/2010 | Hsieh et al. |
| 2011/0015495 | A1 | 1/2011 | Dothie et al. |
| 2011/0018720 | A1* | 1/2011 | Rai ...................... A61B 5/4812 340/575 |
| 2011/0190594 | A1* | 8/2011 | Heit ....................... G16H 20/70 600/26 |
| 2011/0224510 | A1* | 9/2011 | Oakhill ................. A61B 5/4815 600/301 |
| 2011/0230790 | A1 | 9/2011 | Kozlov |
| 2011/0252684 | A1 | 10/2011 | Ufer et al. |
| 2011/0295083 | A1 | 12/2011 | Doelling et al. |
| 2012/0142443 | A1 | 6/2012 | Savarese et al. |
| 2012/0238800 | A1* | 9/2012 | Naujokat ............... A61B 5/318 600/26 |
| 2012/0253220 | A1* | 10/2012 | Rai ........................ A61B 5/369 600/544 |
| 2012/0316455 | A1 | 12/2012 | Rahman et al. |
| 2012/0316471 | A1 | 12/2012 | Rahman et al. |
| 2013/0002435 | A1* | 1/2013 | Utter, II ............... A61B 5/0022 340/575 |
| 2013/0018284 | A1* | 1/2013 | Kahn .................... A61B 5/681 600/595 |
| 2013/0096843 | A1 | 4/2013 | Yuen et al. |
| 2013/0310712 | A1* | 11/2013 | Kanemitsu ........... A61B 5/4812 600/595 |
| 2014/0058703 | A1* | 2/2014 | Kimishima .......... G06Q 10/109 702/177 |
| 2014/0073486 | A1* | 3/2014 | Ahmed ................. A61B 5/441 600/479 |
| 2014/0088378 | A1 | 3/2014 | Muzet |
| 2014/0089243 | A1 | 3/2014 | Oppenheimer |
| 2014/0135594 | A1 | 5/2014 | Yuen et al. |
| 2014/0172362 | A1 | 6/2014 | Burton et al. |
| 2014/0176422 | A1 | 6/2014 | Brumback et al. |
| 2014/0176475 | A1 | 6/2014 | Myers et al. |
| 2014/0180022 | A1 | 6/2014 | Stivoric et al. |
| 2014/0200474 | A1 | 7/2014 | Selvaraj et al. |
| 2014/0275854 | A1 | 9/2014 | Venkatraman et al. |
| 2014/0316305 | A1 | 10/2014 | Venkatraman et al. |
| 2014/0316584 | A1 | 10/2014 | Matsuoka et al. |
| 2014/0347366 | A1* | 11/2014 | Emori ..................... A61B 5/742 345/440 |
| 2014/0364770 | A1 | 12/2014 | Slonneger et al. |
| 2015/0026647 | A1 | 1/2015 | Park et al. |
| 2015/0057967 | A1 | 2/2015 | Albinali |
| 2015/0173167 | A1 | 6/2015 | Lacoste |
| 2015/0173671 | A1 | 6/2015 | Paalasmaa et al. |
| 2015/0355612 | A1* | 12/2015 | Franceschetti ......... G16H 40/67 700/275 |
| 2016/0007934 | A1 | 1/2016 | Arnold et al. |
| 2016/0022175 | A1 | 1/2016 | Arnold et al. |
| 2016/0022201 | A1 | 1/2016 | Arnold et al. |
| 2016/0022203 | A1 | 1/2016 | Arnold et al. |
| 2016/0051184 | A1* | 2/2016 | Wisbey ................. A61B 5/6817 600/595 |
| 2016/0066716 | A1* | 3/2016 | Rao ...................... A61B 5/6814 600/26 |
| 2016/0151603 | A1* | 6/2016 | Shouldice ............ A61B 5/4806 600/26 |
| 2016/0235359 | A1 | 8/2016 | Cho et al. |
| 2016/0246259 | A1* | 8/2016 | Zhang .................... G04B 23/12 |
| 2016/0270718 | A1* | 9/2016 | Heneghan ........ A61M 16/0069 |
| 2017/0094046 | A1* | 3/2017 | Raymann ............. H04L 67/535 |
| 2017/0312477 | A1 | 11/2017 | Hashizaki et al. |
| 2017/0347946 | A1 | 12/2017 | Arnold et al. |
| 2017/0347949 | A1 | 12/2017 | Arnold et al. |
| 2017/0352287 | A1 | 12/2017 | Arnold et al. |
| 2018/0064388 | A1 | 3/2018 | Heneghan et al. |
| 2019/0038185 | A1 | 2/2019 | Arnold et al. |

FOREIGN PATENT DOCUMENTS

| | | |
|---|---|---|
| WO | WO 2012/170586 | 12/2012 |
| WO | WO 2012/170924 | 12/2012 |

(56) References Cited

FOREIGN PATENT DOCUMENTS

| WO | WO 2012/171032 | 12/2012 |
| WO | WO 2015/119726 | 8/2015 |
| WO | WO 2015/127067 | 8/2015 |
| WO | WO 2016/003269 | 1/2016 |
| WO | WO 2018/048951 | 3/2018 |

OTHER PUBLICATIONS

Ribeiro, Pedro Ramiro Guimaraes, "Sensor based sleep patterns and nocturnal activity analysis," Faculdade de Engenharia da Universidade do Porto, Jul. 17, 2014, 38 pages.
U.S. Office Action, dated Dec. 15, 2016, issued in U.S. Appl. No. 15/171,049.
U.S. Final Office Action, dated Jun. 15, 2017, issued in U.S. Appl. No. 15/171,049.
U.S. Office Action, dated May 3, 2018, issued in U.S. Appl. No. 15/171,049.
U.S. Notice of Allowance, dated Dec. 31, 2018, issued in U.S. Appl. No. 15/171,049.
U.S. Office Action, dated Nov. 30, 2016, issued in U.S. Appl. No. 15/192,455.
U.S. Final Office Action, dated Jun. 21, 2017, issued in U.S. Appl. No. 15/192,455.
U.S. Office Action, dated May 14, 2018, issued in U.S. Appl. No. 15/192,455.
U.S. Notice of Allowance, dated Dec. 31, 2018, issued in U.S. Appl. No. 15/192,455.
U.S. Office Action, dated Dec. 28, 2016, issued in U.S. Appl. No. 15/199,113.
U.S. Final Office Action, dated Jul. 28, 2017, issued in U.S. Appl. No. 15/199,113.
U.S. Office Action, dated Mar. 6, 2019, issued in U.S. Appl. No. 15/438,643.
U.S. Office Action, dated Jun. 24, 2016, issued in U.S. Appl. No. 14/859,192.
U.S. Office Action, dated Feb. 8, 2017, issued in U.S. Appl. No. 14/859,192.
U.S. Notice of Allowance, dated Aug. 17, 2017, issued in U.S. Appl. No. 14/859,192.
U.S. Office Action, dated Apr. 18, 2016, issued in U.S. Appl. No. 14/877,912.
U.S. Final Office Action, dated Dec. 1, 2016, issued in U.S. Appl. No. 14/877,912.
U.S. Office Action, dated Jul. 24, 2017, issued in U.S. Appl. No. 14/877,912.
U.S. Office Action, dated Jan. 25, 2018, issued in U.S. Appl. No. 14/877,912.
U.S. Notice of Allowance, dated May 11, 2018, issued in U.S. Appl. No. 14/877,912.
U.S. Office Action, dated Apr. 22, 2016, issued in U.S. Appl. No. 14/877,920.
U.S. Final Office Action, dated Aug. 30, 2016, issued in U.S. Appl. No. 14/877,920.
U.S. Notice of Allowance, dated Feb. 13, 2017, issued in U.S. Appl. No. 14/877,920.
U.S. Office Action, dated Jun. 1, 2016, issued in U.S. Appl. No. 14/877,922.
U.S. Final Office Action, dated Nov. 16, 2016, issued in U.S. Appl. No. 14/877,922.
U.S. Office Action, dated Mar. 11, 2019, issued in U.S. Appl. No. 16/058,423.
U.S. Final Office Action, dated Jul. 30, 2019, issued in U.S. Appl. No. 16/058,423.
International Search Report and Written Opinion—PCT/US17/50344—ISA/EPO—dated Mar. 2, 2018.
International Preliminary Report on Patentability—PCT/US17/50344—ISA/EPO—Mar. 21, 2019.

\* cited by examiner

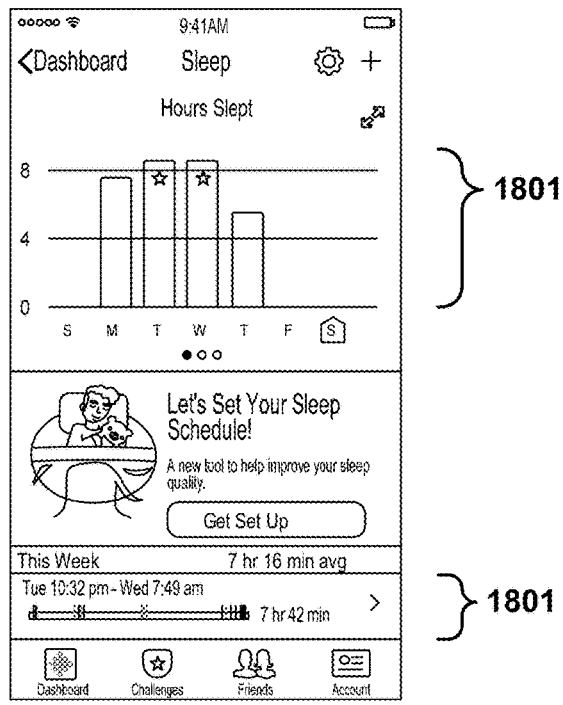
Figure 18
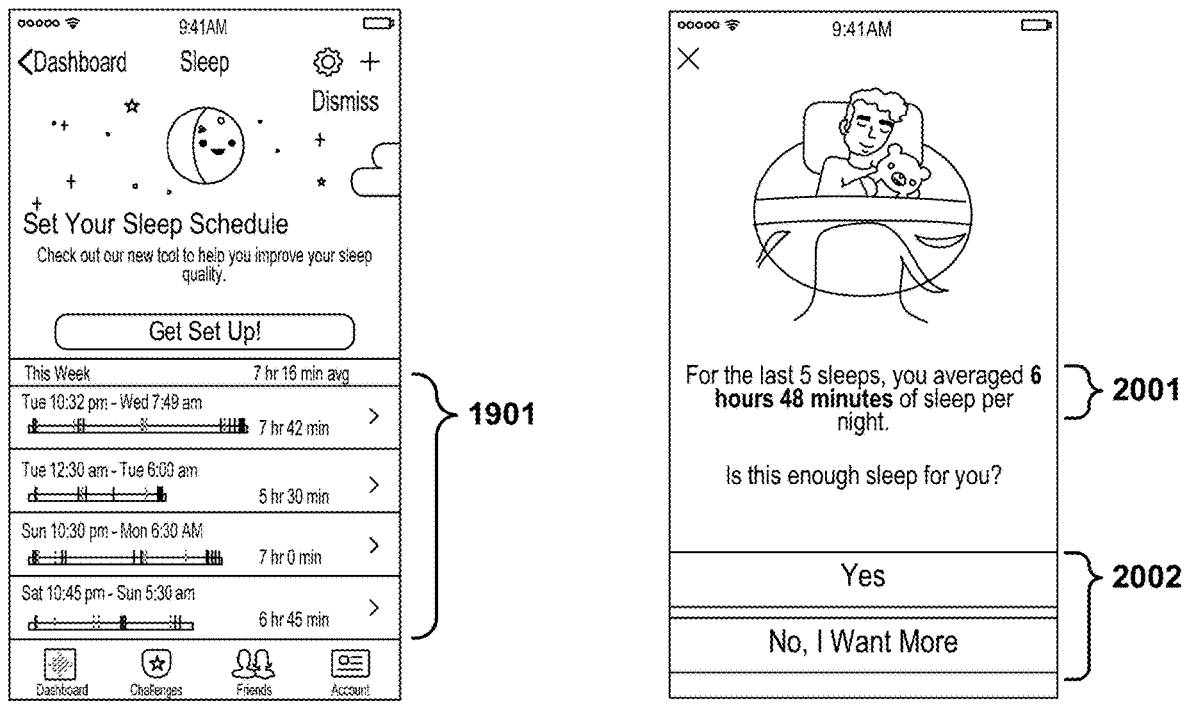
Figure 19
Figure 20

SYSTEMS AND TECHNIQUES FOR TRACKING SLEEP CONSISTENCY AND SLEEP GOALS

CROSS-REFERENCE TO RELATED APPLICATION

This application is a continuation application under 35 U.S.C. § 120 of U.S. patent application Ser. No. 15/171,049, filed Jun. 2, 2016, now U.S. Pat. No. 10,325,514, issuing Jun. 18, 2019, which is hereby incorporated by reference in its entirety for all purposes.

BACKGROUND

Personal fitness and health monitoring devices, which may be referred to as biometric monitoring devices herein, may include a variety of different sensors that are used to provide feedback regarding various physiological characteristics of a person. Such sensors may be used to track sleep of a user.

SUMMARY

Details of one or more implementations of the subject matter described in this specification are set forth in the accompanying drawings and the description below. Other features, aspects, and advantages will become apparent from the description, the drawings, and the claims.

In one embodiment, a method of generating one or more personalized graphical user interfaces for setting a sleep schedule of a user of a biometric monitoring device may be provided. The method may include obtaining sleep data derived from sensor data generated by the biometric monitoring device, the sleep data including data regarding a plurality of sleep sessions and specifying various sleep states of the user for the respective sleep sessions; storing the sleep data in a sleep log data store as one or more sleep logs associated with an account assigned to the user, the sleep log data store also including sleep logs including sleep data derived from sensor data generated by other biometric monitoring devices of other users; and causing the one or more personalized graphical user interfaces to be displayed to the user. Causing the one or more personalized graphical user interfaces to be displayed to the user may include obtaining a scheduled waketime of the user, obtaining a recommended bedtime based on a calculation accounting for, at least in part, the scheduled waketime and a sleep efficiency based on the sleep data for one or more users stored in the sleep log data store, and causing the recommended bedtime to be displayed in a graphical user interface element of at least one of the one or more personalized graphical user interfaces.

In some embodiments, causing the one or more personalized graphical user interfaces to be generated may further include obtaining a selected sleep duration of the user, and calculating the recommended bedtime may be further based on the selected sleep duration of the user.

In some embodiments, causing the one or more personalized graphical user interfaces to be generated may further include obtaining timing information indicating one or more selected reminder times for a bedtime reminder, and the method may further include generating the bedtime reminder based on the timing information.

In some further embodiments, the bedtime reminder may include information regarding the recommended bedtime.

In some other further embodiments, causing the one or more personalized graphical user interfaces to be generated may further include calculating a recommended reminder time for the bedtime reminder based on the recommended bedtime and causing the recommended reminder time to be displayed in a graphical user interface element of the one or more personalized graphical user interfaces.

In some other further embodiments, causing the one or more personalized graphical user interfaces to be generated may further include obtaining day information indicating one or more selected reminder days for the bedtime reminder, and the generating of the bedtime reminder may be further based on the day information.

In some other further embodiments, the method may further include providing the bedtime reminder via a notification such as a message, an auditory output, an electronic communication, an electromagnetic communication, a visual output, or a tactile output.

In some embodiments, causing the one or more personalized graphical user interfaces to be generated may further include determining whether sleep state duration data of the user that is representative of the time the user spent in one or more non-awake sleep states during one of the sleep sessions of the user is within a threshold of the selected sleep duration, and causing information associated with the determination to be displayed in a graphical user interface element of at least one of the one or more personalized graphical user interfaces.

In some further embodiments, causing the information associated with the determination to be displayed may include causing a timeline to be displayed showing a graphical indication of the threshold relative to the timeline and a graphical indication of the sleep state duration data relative to the timeline.

In some other further embodiments, causing the one or more personalized graphical user interfaces to be generated may further include causing, based on a determination that the sleep state duration data of the user is not within the threshold of the selected sleep duration, one or more of: a second recommended bedtime, a recommended sleep duration, and a recommended waketime to be displayed in a graphical user interface element of at least one of the one or more personalized graphical user interfaces.

In some other further such embodiments, the one or more of the second recommended bedtime, the recommended sleep duration, and the recommended waketime that are displayed in the graphical user interface element may be, respectively, different from the recommended bedtime by a first time increment, different from the selected sleep duration by a second time increment, and different from the scheduled waketime by a third time increment.

In some embodiments, causing the one or more personalized graphical user interfaces to be generated may further include calculating a recommended waketime based on waketimes derived from the sleep data for the user stored in the sleep log data store and causing the recommended waketime to be displayed in a graphical user interface element of at least one of the one or more personalized graphical user interfaces.

In some further embodiments, obtaining the recommended bedtime may be further based on the recommended waketime.

In some embodiments, causing the one or more personalized graphical user interfaces to be generated may further include calculating a recommended sleep duration based on the sleep data for one or more users stored in the sleep log data store, and causing the recommended sleep duration to be displayed in a graphical user interface element of at least one of the one or more personalized graphical user interfaces.

In some further embodiments, obtaining the recommended bedtime may be further based on the recommended sleep duration.

In some embodiments, causing the one or more personalized graphical user interfaces to be generated may further include determining, based on the sleep data of the user, whether a waketime of the user for one of the sleep sessions of the user is within a threshold of the scheduled waketime, and causing information associated with the determination to be displayed in a graphical user interface element of at least one of the one or more personalized graphical user interfaces.

In some further embodiments, causing the information associated with the determination to be displayed may include causing a timeline to be displayed showing a graphical indication of the threshold relative to the timeline and a graphical indication of the waketime relative to the timeline.

In some other further embodiments, causing the one or more personalized graphical user interfaces to be generated may further include causing, based on a determination that the waketime of the user is not within the threshold of the scheduled waketime, one or more of a second recommended bedtime, a recommended sleep duration, and a recommended waketime to be displayed in a graphical user interface element of at least one of the one or more personalized graphical user interfaces.

In some other further such embodiments, the one or more of the second recommended bedtime, the recommended sleep duration, and the recommended waketime that are displayed in the graphical user interface element may be, respectively, different from the recommended bedtime by a first time increment, different from the selected sleep duration by a second time increment, and different from the scheduled waketime by a third time increment.

In some embodiments, causing the one or more personalized graphical user interfaces to be generated may further include determining, based on the sleep data of the user, whether a bedtime of the user for one of the sleep sessions of the user is within a threshold of the scheduled bedtime, and causing information associated with the determination to be displayed in a graphical user interface element of at least one of the one or more personalized graphical user interfaces.

In some further embodiments, causing the information associated with the determination to be displayed may include causing a timeline to be displayed showing a graphical indication of the threshold relative to the timeline and a graphical indication of the bedtime relative to the timeline.

In some other further embodiments, causing the one or more personalized graphical user interfaces to be generated may further include causing, based on a determination that the bedtime of the user is not within the threshold of the scheduled bedtime, one or more of a second recommended bedtime, a recommended sleep duration, and a recommended waketime to be displayed in a graphical user interface element of at least one of the one or more personalized graphical user interfaces.

In some other further embodiments, the one or more of the second recommended bedtime, the recommended sleep duration, and the recommended waketime that are displayed in the graphical user interface element may be, respectively, different from the recommended bedtime by a first time increment, different from the selected sleep duration by a second time increment, and different from the scheduled waketime by a third time increment.

In some embodiments, the sleep efficiency may be representative, at least in part, of a correlation between sleep state duration data for one or more sleep sessions stored in the sleep log data store and sleep session duration data for the corresponding plurality of sleep sessions, the sleep state duration data may be representative of the total amount of time the user that is associated with the sleep session spent in a subset of non-awake sleep states during the sleep session, and the sleep session duration data may be representative of the total duration of the sleep session.

In some embodiments, the method may further include, prior to obtaining the recommended bedtime and causing the recommended bedtime to be displayed in the graphical user interface element of the at least one of the one or more personalized graphical user interfaces determining that the user is a new user without sleep data stored in the sleep log data store, and causing a suggested sleep duration to be displayed in a graphical user interface element of at least one of the one or more personalized graphical user interfaces. The suggested sleep duration may based on one or more of a default value and a target sleep duration determined based on one or more of the sleep logs including sleep data derived from the sensor data generated by the other biometric monitoring devices of the other users.

In some embodiments, the method may further include determining that a first number of sleep logs associated with the account assigned to the user exist in the sleep log data store, and the causing the one or more personalized graphical user interfaces to be displayed may occur after the determination.

In one embodiment, a system for setting a sleep schedule of a user of a biometric monitoring device may be provided. The system may include one or more processors and a memory. The one or more processors may be communicatively connected with the memory, and the memory may store instructions that, when executed, cause the one or more processors to obtain sleep data derived from sensor data generated by the biometric monitoring device, the sleep data including data regarding a plurality of sleep sessions and specifying various sleep states of the user for the respective sleep sessions; store the sleep data in a sleep log data store as one or more sleep logs associated with an account assigned to the user, the sleep log data store also storing other sleep logs including other sleep data derived from other sensor data generated by other biometric monitoring devices of other users; and calculate a target bedtime based on a scheduled waketime of the user and a sleep efficiency derived, at least in part, from the sleep data for one or more users stored in the sleep log data store.

In some embodiments, the target bedtime may be based on the sleep efficiency of the other users of the other biometric monitoring devices. In some other embodiments, the target bedtime may be based on the sleep efficiency of the user of the biometric monitoring device.

In some embodiments, the memory may further store instructions that, when executed, cause the one or more processors to obtain sleep state duration data for a sleep session stored in the sleep log data store, the sleep state duration data being representative of the total amount of time the user that is associated with the sleep session spent in one or more sleep states during the sleep session, determine sleep session duration data for the sleep session stored in the sleep log data store, the sleep session duration data being representative of the total time of that sleep session. The sleep efficiency may be representative, at least in part, of a correlation between sleep state duration data for one or more sleep sessions and sleep session duration data for the corresponding one or more sleep sessions.

In some further embodiments, the memory may further store instructions for controlling the one or more processors to obtain the scheduled waketime of the user from the user via a graphical user interface.

In some other further embodiments, the calculation of the target bedtime may be further based on the sleep efficiency of the user.

In some other further embodiments, the calculation of the target bedtime may be further based on a selected sleep duration of the user for a sleep session.

In some other further embodiments, the memory may further store instructions for controlling the one or more processors to obtain the selected sleep duration of the user for the sleep session.

In some such embodiments, the memory may further store instructions for controlling the one or more processors to determine a regression model that relates the sleep session duration data for a plurality of sleep sessions stored in the sleep log data store to corresponding sleep state duration data for the plurality of sleep sessions, and the calculation of the target bedtime may be further based on the regression model.

In some further such embodiments, the sleep efficiency for each sleep session may be calculated, at least in part, by dividing the sleep state duration data for that sleep session by the sleep session duration data for that sleep session.

In some other further such embodiments, the plurality of sleep sessions may be for the other users of the other biometric monitoring devices.

In some other further such embodiments, the regression model may be a regression model such as a linear regression model, a nonlinear regression model, a parametric regression model, a nonparametric regression model, a semiparametric regression model, and a multivariate linear regression model.

In some other further such embodiments, the sleep session duration data and corresponding sleep state duration data for the plurality of sleep sessions that may be included in the regression model are associated with sleep sessions with waketimes that are within a first threshold amount of the scheduled waketime.

In some other further such embodiments, the sleep session duration data and corresponding sleep state duration data for the plurality of sleep sessions that may be included in the regression model are associated with sleep state duration data that are within a second threshold amount of the selected sleep duration.

In some other further such embodiments, the sleep session duration data and corresponding sleep state duration data for the plurality of sleep sessions that may be included in the regression model are associated with sleep sessions with waketimes that have occurred on the same day of the week as the day of the week on which the scheduled waketime occurs.

In some other further such embodiments, the regression model may account for one or more of one or more specific days of the week, a specific time of year, holidays, workdays of the user, non-workdays of the user, a seasonal time change, a geographic location, travel by the user between at least two time zones, exercise of the user, and a duration of daylight in a day.

In some embodiments, the sleep efficiency for each sleep session may be calculated, at least in part, by dividing the sleep state duration data for each sleep session by the sleep session duration data for each corresponding sleep session, respectively, and the sleep efficiency may be accounted for, at least in part, by multiplying the selected sleep duration by a factor that is based on the sleep efficiencies for the plurality of sleep sessions to determine a predicted sleep session duration.

In some other embodiments, the memory may store instructions for further controlling the one or more processors to cause a notification mechanism to produce a notification relating to a comparison of sleep state duration data for one or more sleep sessions with the selected sleep duration data.

In some embodiments, the memory may store instructions for further controlling the one or more processors to determine a recommended bedtime based on the target bedtime. The recommended bedtime may be further based on one or more of one or more specific days of the week, a specific time of year, holidays, workdays of the user, non-workdays of the user, a seasonal time change, a geographic location, travel by the user between at least two time zones, exercise of the user, and a duration of daylight in a day.

In some embodiments, the sleep efficiency may be further based on of historical sleep efficiency data associated with one or more of a proper subset of one or more specific days of the week, a time of year, holidays, workdays of the user, non-workdays of the user, a seasonal time change, a geographic location, travel by the user between at least two time zones, exercise of the user, and a duration of daylight in a day.

In some embodiments, the system may further include the biometric monitoring device that includes one or more sensors configured to generate the sensor data, and a communications interface to communicate the sensor data to the one or more processors.

BRIEF DESCRIPTION OF THE DRAWINGS

The various implementations disclosed herein are illustrated by way of example, and not by way of limitation, in the figures of the accompanying drawings, in which like reference numerals refer to similar elements.

FIG. 18 is an example of a graphical user interface that may be used to convey sleep performance data to a user.

FIG. 19 is an example of a graphical user interface that may be used to introduce a user to sleep scheduling features.

FIG. 20 is an example of a graphical user interface that may be used to present typical sleep duration of the user and inquire whether that amount of sleep duration is sufficient.

DETAILED DESCRIPTION

Figure 1:
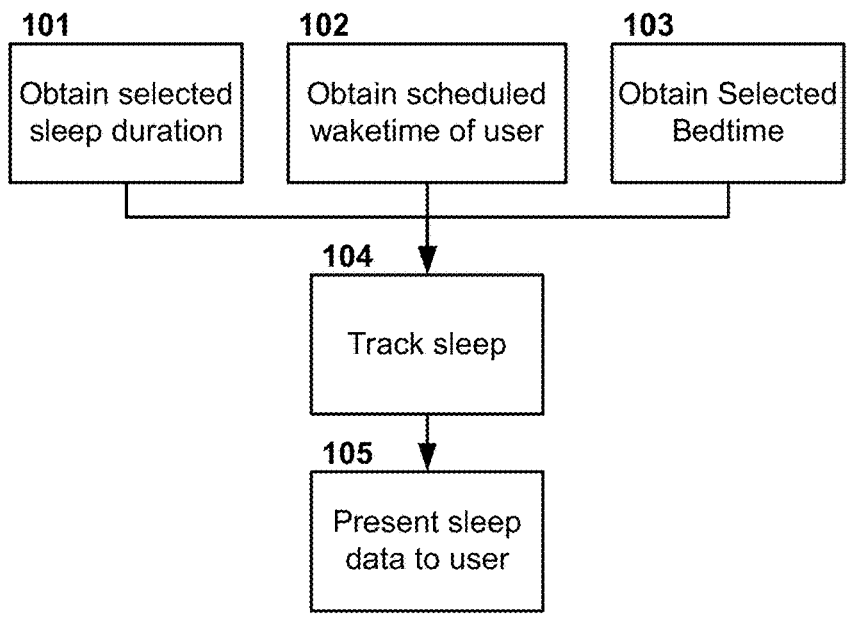
FIG. 1 depicts a high-level flow diagram of sleep scheduling and sleep tracking techniques discussed herein.

An aspect of the present disclosure relates to assisting and guiding users to set goals that promote consistent sleep behavior. Consistent sleep behavior is a foundation of healthy sleep due in part to its relation to the circadian rhythm which regulates many bodily functions, including sleep. For example, this rhythm affects when a person is awake, aware, tired, and ready to sleep. The more regular a person's sleep cycles are, the easier it may be for the person's body to function in accordance with the circadian rhythm. Consistent sleep behavior, which may include a consistent waketime, bedtime, and/or sleep duration, helps establish this rhythm and keep a person's sleep well patterned and healthy. The present disclosure is directed to methods, techniques, apparatuses, systems, and the like which help guide a user to set goals for sleep duration, wakeup time, and/or bedtime that will in turn help establish consistent sleep behaviors. Some of the techniques discussed in this disclosure utilize "sleep tracking," which includes the monitoring, i.e., tracking, of a user's sleep by, at least in part, analyzing sleep data that is derived from sensor data generated by a biometric monitoring device, in order to better guide a person to a more consistent sleep cycle. The present inventors have determined that the methods, techniques, apparatuses, systems, and the like disclosed herein may, in some cases, be used to promote better sleep consistency and improve the sleep of users.

As noted above, one factor for consistent sleep behavior is sleep duration of the user for a given sleep session; however, each person does not require the same sleep duration. For example, while a typical sleep duration recommendation for adults is 7-9 hours of sleep, different people may need different sleep durations in order to be healthy, productive, and/or to feel rested. Therefore, the present disclosure is intended, at least in part, to determine, recommend, and/or set an individualized or personalized recommended sleep duration for each user. Further, some of the embodiments described herein may provide recommended sleep duration with higher fidelity as compared to the two hour window provided by a generic recommendation of 7-9 hours of sleep. For example, the embodiments described herein may generate a sleep duration recommendation that is, in some cases, a range of durations (e.g., 8+/−0.5 hours) or, in other cases, a specific duration (e.g., 8 hours).

A "sleep session," as used herein, may generally be considered data and/or logic that represents a period of time during which an individual is attempting to sleep or is actually sleeping. The precise data or logic of a sleep session may vary depending on a variety of factors. For example, the start time and end time of a sleep session may be established according to a variety of different techniques. For example, the start time of a sleep session may be derived from sensors when an individual first enters a bed in an attempt to sleep (such as may be measured by a biometric monitoring device that includes a pressure sensor located in a bed—if the sensor detects pressure commensurate with the presence of the individual, then the biometric monitoring device may determine that the individual in bed and is attempting to sleep), when the individual manually indicates to a biometric monitoring device the beginning of a sleep session (such as by pressing a button on a biometric monitoring device to indicate the start of a sleep session), and/or when a processor has determined, from data generated by, for instance, the biometric monitoring device, that a person has engaged in behavior indicative of the start of a sleep session (e.g., by remaining generally motionless for an extended period of time, such as may be detected by accelerometers or other motion sensors in the biometric monitoring device).

In some cases, the start of a sleep session may be contemporaneous or near-contemporaneous with when a person actually falls asleep. For example, if data from a wearable biometric monitoring device worn by an individual indicates that the person has transitioned from an awake state to an asleep state (without any data indicating that the individual is trying to go to sleep beforehand), then such a transition may be deemed to be the start or beginning of the sleep session. Similarly, for example, the sleep session may end when a person exits a bed, when the individual manually inputs to the biometric monitoring device the end of the sleep session, and/or when the processor has determined, from data generated by the biometric monitoring device, that the person has stopped sleeping (for example, accelerometers in the biometric monitoring device indicate that the person is walking or otherwise engaged in prolonged movement). In some embodiments, each sleep session may be bounded by a respective bedtime of the user and respective waketime of the user. It is to be understood that a sleep session may be punctuated by periods of wakefulness or restlessness—for example, an individual may get up to go to the bathroom, let a pet out, or nurse a baby. Such short periods of wakefulness, when followed by a return to sleep, would not be viewed as the "end" of a sleep session. As will be clear, the exact start and end times of a sleep session may be subject to some variability depending on what criteria are used to determine such parameters; it is to be understood that the concepts and techniques discussed herein may be practiced using any of a variety of such different definitions of what a sleep session is. In the context of computing or processing systems that be used to implement the techniques and methods discussed herein and to collect physiological data, e.g., heart rate, movement, breathing rate, etc., of an individual during sleep and log such data, the term "sleep session" is to be understood to refer to the window of time that such a computing or processing system establishes as being representative of the individual's actual sleep session. The duration of a sleep session, which may include periods of both sleep and wakefulness, as described above, is referred to herein as the "sleep session duration."

The biometric monitoring devices that may be used to collect biometric sensor data, e.g., physiological data, that may be evaluated to determine one or more types of sleep data usable with the techniques discussed herein may be wearable biometric monitoring devices, e.g., such as a wrist-wearable fitness tracker such as the Fitbit™ Charge™, Surge™, or other similar device; non-wearable biometric monitoring devices, such as sleep-monitoring sensor systems that are integrated into a mattress pad, mattress, or similar bed-integrated system or that are configured to operate from a location remote from a bed, e.g., such as a nightstand adjacent to a bed; or combinations thereof.

As an individual sleeps or prepares to sleep, the embodiments discussed herein may detect that the individual passes through a variety of different states, such as an awake state, an asleep state, a waking state (in which the individual is transitioning from an asleep state to an awake state), etc. At a minimum, the embodiments may determine that an individual is in one of at least two states, "awake" and "asleep," at one or more given times during a sleep session. In some cases, additional determinations may be made to identify when an individual is in one or more other sleep states, e.g., a restless state, a waking or starting-to-wake state, etc. Moreover, in some implementations, sleep states may be further granularized into multiple sleep stages or sleep phases. For example, an asleep state may include one or more periods when the individual is in stage 1, e.g., NREM1, N1, somnolence, light, or drowsy sleep) sleep, one or more further periods where the individual is in stage 2, e.g., NREM2 or N2) sleep, one or more further periods where the individual is in stage 3, e.g., NREM3, N3, deep, delta, or slow-wave sleep) sleep, and one or more periods of random eye movement (REM) sleep; it is not necessarily the case that an individual will pass through all of these stages of sleep in any given sleep session—each of these sleep stages may also be viewed as a type of sleep state or as part of a sleep state (if a sleep state includes time spent in multiple sleep stages). An individual's sleep duration is a characterization of the amount of time that that individual spends in one or more sleep states other than the awake state during a sleep session. The sleep states of interest for determining sleep duration (which may also be referred to herein as "sleep state duration") may include sleep states that represent one or more of the different stages of sleep. In some cases, sleep duration may simply be a measure of how much time a given individual is asleep during a sleep session—regardless of whether the individual is experiencing restless, light, deep, or REM sleep. In other cases, such a system may be configured to only credit time spent in deep or REM sleep towards an individual's sleep duration. Thus, sleep state duration may, in some implementations, be inclusive of all of the time that a user spent in any of the non-awake sleep states. The sleep state duration may, in other implementations, be inclusive of all of the time that a user spent in a non-empty proper subset of the non-awake sleep states.

As noted above, the user's sleep duration, including the time spent in various sleep states, as well as other sleep-related information about the user, may be determined and/or obtained from sleep data derived from sensor data generated by a biometric monitoring device. For example, the biometric monitoring device may include a plurality of sensors which are configured to generate data indicative of the movements and physiological state of the user; when the user wears the biometric monitoring device to bed, at least some of the biometric monitoring device's sensors may generate data that is collected and analyzed by one or more processors to derive sleep data from this sensor data. The sensors collecting such data may be, for instance, a motion sensor like a multi-axis accelerometer or an optical heart rate monitor module including a photoplethysmographic sensor. The generated sensor data may include, for instance, movement data of the user or heart rates of the user. The generated sensor data may be analyzed and/or categorized into sleep data, which may include, for example, the sleep duration, sleep states, sleep stages, sleep state duration, sleep session duration, waketime, and/or bedtime of the user for each sleep session—for example, various Fitbit™ biometric monitoring devices, such as the Charge™, Charge HR™, Pulse™, utilize accelerometer data to track a person's movement during sleep and identify periods or epochs during which the person is awake, restless, or awake. Sleep data may also include various biometric measurements that, while not directly related to sleep, may nonetheless be useful in determining various sleep-related data, e.g., heart rate (heart rate may indicate, in part, a particular sleep state or sleep stage of a person), respiratory rate (respiratory rate may also indicate, in part, a particular sleep state or sleep stage of a person), movement levels, etc. Based on this data, a total sleep session duration, total amount of time actually spent asleep, and total amount of time spent awake or restless may be determined. For example, for a given sleep session, the sleep data for that session may indicate that the individual went to bed at 11:06 PM and woke up at 6:33 AM (for a sleep session duration of 7 hours and 27 minutes), was restless 15 times during the night, woke up 3 times, spent 37 minutes total in an awake or restless state, and was actually asleep for 6 hours and 50 minutes. It is to be understood that "based on," in the context of this disclosure, also means "based, at least in part, on," and that these two phrases may be used interchangeably. Moreover, it is to be understood that in instances where "based on" or "based, at least in part, on" are used, one of the implementations that is embraced by such language, unless the context of such usage indicates otherwise, is the singular case, e.g., where a determination of a parameter is "based exclusively on" a particular type of data. For example, if a parameter A is calculated based on (or based, at least in part, on) a parameter B, this is to be understood as encompassing situations in which parameter A may be calculated solely based on parameter B as well as situations in which parameter A may be calculated based on parameter B in combination with other parameters, such as parameter(s) C (and D).

For example, the biometric monitoring device's sensors may generate movement data of the user which may be analyzed by one or more processors to determine a user's sleep state, e.g., based on sleep stage or on other determinations without reference to a particular sleep stage, such as overall restlessness. One such analysis may include the generation of a movement measure or sleep coefficient based on, at least in part, the movement data that is collected for a period of time, e.g., 30 seconds. Then, based on the movement measure of a larger period of time, e.g., a window of time larger than the period of time, an activity level of the user is calculated; the activity level may be active or inactive. A user's sleep state may then be classified based, at least in part, on the activity levels of the user calculated for a contiguous time period over a number of windows of time.

A further example of obtaining, measuring, and/or determining sleep data, such as a user's sleep duration and sleep states, is more fully described in U.S. patent application Ser. No. 14/859,192, filed Sep. 18, 2015, titled "Movement Measure Generation In A Wearable Electronic Device", which is hereby incorporated herein by reference for all purposes.

Some techniques of the present disclosure include generating one or more personalized graphical user interfaces for setting a sleep schedule of a user of a biometric monitoring device. At least some of the graphical user interfaces may be generated in a display of the biometric monitoring device while at least some others may be generated in a display of an electronic device such as a smartphone, tablet, and/or personal computer.

As noted earlier, the techniques and systems discussed herein may be used to guide users of biometric monitoring devices to engage in more consistent sleep behavior.

FIG. 1 depicts a high-level flow diagram of sleep scheduling and sleep tracking techniques as discussed in more detail below. As can be seen in FIG. 1, the overall technique may involve obtaining, through various mechanisms, one or more parameters affecting an individual's sleep schedule—for example, obtaining one or more of a selected sleep duration 101, a scheduled waketime 102, and a selected bedtime 103 may be obtained through one or more different techniques, as discussed in more detail below. After one or more of such parameters have been obtained, the individual's sleep may be tracked 104 to determine various characteristics of the person's sleep behaviors, which may be stored as sleep data. The sleep data may be used for a variety of purposes, including for presentation 105 to the individual and for providing personalized recommended bedtimes, as discussed in more detail later.

The various sleep parameters that are obtained, e.g., selected sleep duration, scheduled waketime, and selected bedtime, may be obtained relatively simultaneously, e.g., by a user entering all three parameters into a common user interface (see, for example, the GUI of FIG. 38, which is discussed later), or in a staged or staggered manner. For example, for an individual who is new to sleep tracking or who has not previously set up sleep tracking on a biometric monitoring device, a selected sleep duration may first be obtained and then the individual's sleep may then be tracked in order to determine how consistently the individual is meeting such a sleep duration goal—at some later point, further sleep parameters may be obtained, such as the individual's scheduled waketime and selected bedtime. Such a staged progression may allow for the gradual introduction of the individual to the concept of sleep tracking and scheduling, and may serve to be a more effective mechanism for encouraging more consistent sleep behavior. Alternatively, if a user waits for some period of time before exploring the sleep tracking functionality of their biometric monitoring device, the biometric monitoring device may nonetheless collect sleep data for the user if the user wears it bed. Thus, when the user initially explores the sleep tracking functionality, the biometric monitoring device may already have collected some initial sleep data that may be used to suggest a selected sleep duration that is based on the user's actual sleep behavior. In a further variation, a user's past sleep data that was collected with another biometric monitoring device may be used in place of sleep data collected with the biometric monitoring device being set up, and a selected sleep duration (and other parameters) may be provided based on such earlier-collected sleep data.

Figure 2:
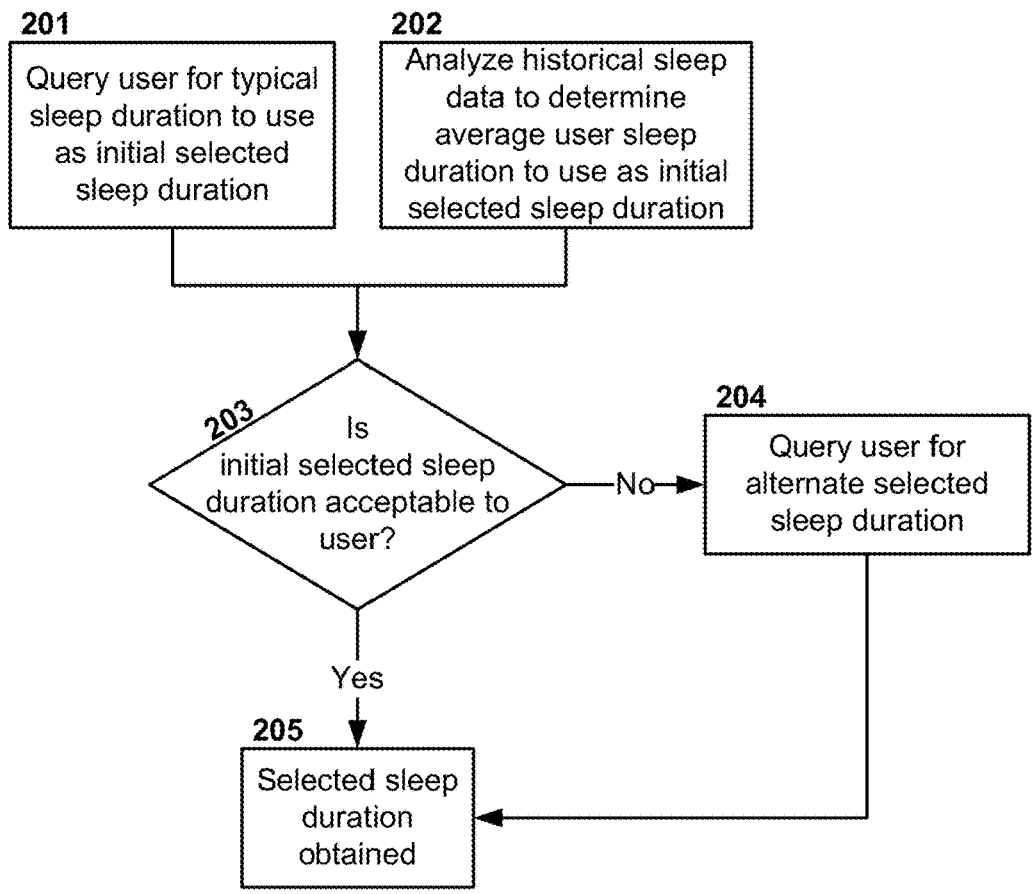
FIG. 2 depicts a high-level flow diagram that outlines techniques for obtaining a selected sleep duration of an individual.

FIG. 2 depicts a high-level flow diagram that outlines techniques for obtaining a selected sleep duration of an individual. To start with, an initial selected sleep duration may be obtained, e.g., by querying the individual to enter a typical sleep duration (as estimated and reported by the individual) in block 201 or by analyzing historical sleep data of the individual in block 202 to determine, for example, an average sleep duration for the individual for some period of time. Once an initial selected sleep duration has been obtained, it may optionally be used directly as the selected sleep duration or may, for example, be subject to modification. For example, the initial selected sleep duration may be presented to the individual and the individual may be prompted in block 203 to indicate if the initial selected sleep duration is acceptable or if the individual wishes to change it. If the individual indicates that the initial selected sleep duration is acceptable, then the initial selected sleep duration may be used as the selected sleep duration in block 205. If the individual indicates the initial selected sleep duration is not acceptable, then the individual may be queried in block 204 for an alternate selected sleep duration. Once the individual has either confirmed the initial selected sleep duration as the selected sleep duration or selected an alternate selected sleep duration, the selected sleep duration may be considered to be obtained in block 205.

As mentioned earlier, an individual's actual sleep duration may be tracked, e.g., via sleep data obtained from a biometric monitoring device, in order to determine to what degree the individual's actual sleep duration correlates with the individual's selected sleep duration. In some implementations, the individual may be prompted to re-evaluate their selected sleep duration to determine if a more achievable selected sleep duration should be selected—for example, if the individual is consistently sleeping only 6 hours a night but has a selected sleep duration of 7 hours, then the individual may be prompted to select a lower selected sleep duration initially. If the individual's sleep data then indicates a subsequent increase in the individual's actual sleep duration, then the individual may be intermittently encouraged to raise the selected sleep duration, e.g., by 15 minutes or 30 minutes at a time, in order to gradually reach the original selected sleep duration.

Once a selected sleep duration for an individual has been obtained, such information may eventually be used with an obtained scheduled waketime and collected sleep data in order to provide a recommended bedtime.

Figure 3:
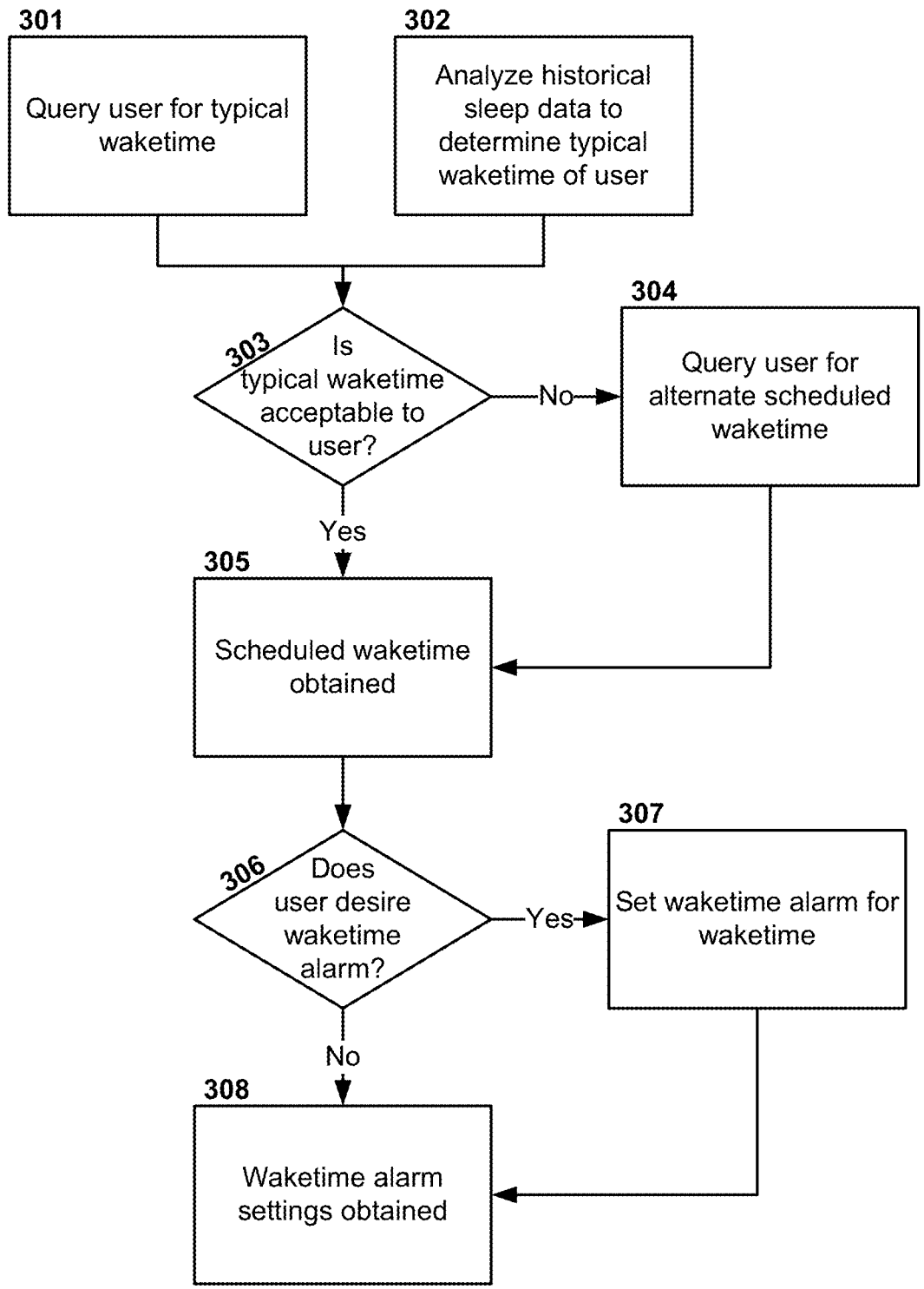
FIG. 3 depicts a high-level flow diagram of techniques for obtaining a scheduled waketime.

FIG. 3 depicts a high-level flow diagram of techniques for obtaining a scheduled waketime. To begin with, the individual may be queried in block 301 to provide a typical waketime, e.g., the time at which the individual normally wakes up, or, alternatively (or additionally), the individual may be presented in block 302 with a typical waketime, e.g., an average waketime, as determined from historical sleep data of the individual. After the typical waketime is obtained, the typical waketime may optionally be presented to the individual and the individual prompted to confirm whether or not the typical waketime is acceptable to the individual in block 303. If the individual indicates in block 303 that the typical waketime is not acceptable in block 303, the individual may be prompted to select an alternate scheduled waketime in block 304, which may then be used as the scheduled waketime in block 306. If the individual indicates in block 303 that the typical waketime is acceptable, then the typical waketime may be used as the scheduled waketime in block 305. Once the scheduled waketime has been obtained, then, in some implementations, the technique may optionally also include configuring a waketime alarm. For example, in block 306, the individual may be presented with a query as to whether or not the individual wishes to set a waketime alarm. If the individual indicates that they wish to set a waketime alarm in block 306, a waketime alarm, e.g., an audible alarm on a smartphone or a vibratory alarm on a wearable biometric monitoring device, may be set to activate at the scheduled waketime in block 307 before the waketime alarm settings may be considered obtained in block 308. If the individual indicates that no waketime alarm is to be set in block 306, then the waketime alarm settings may be considered to be obtained (with no alarm set) in block 308.

Figure 4:
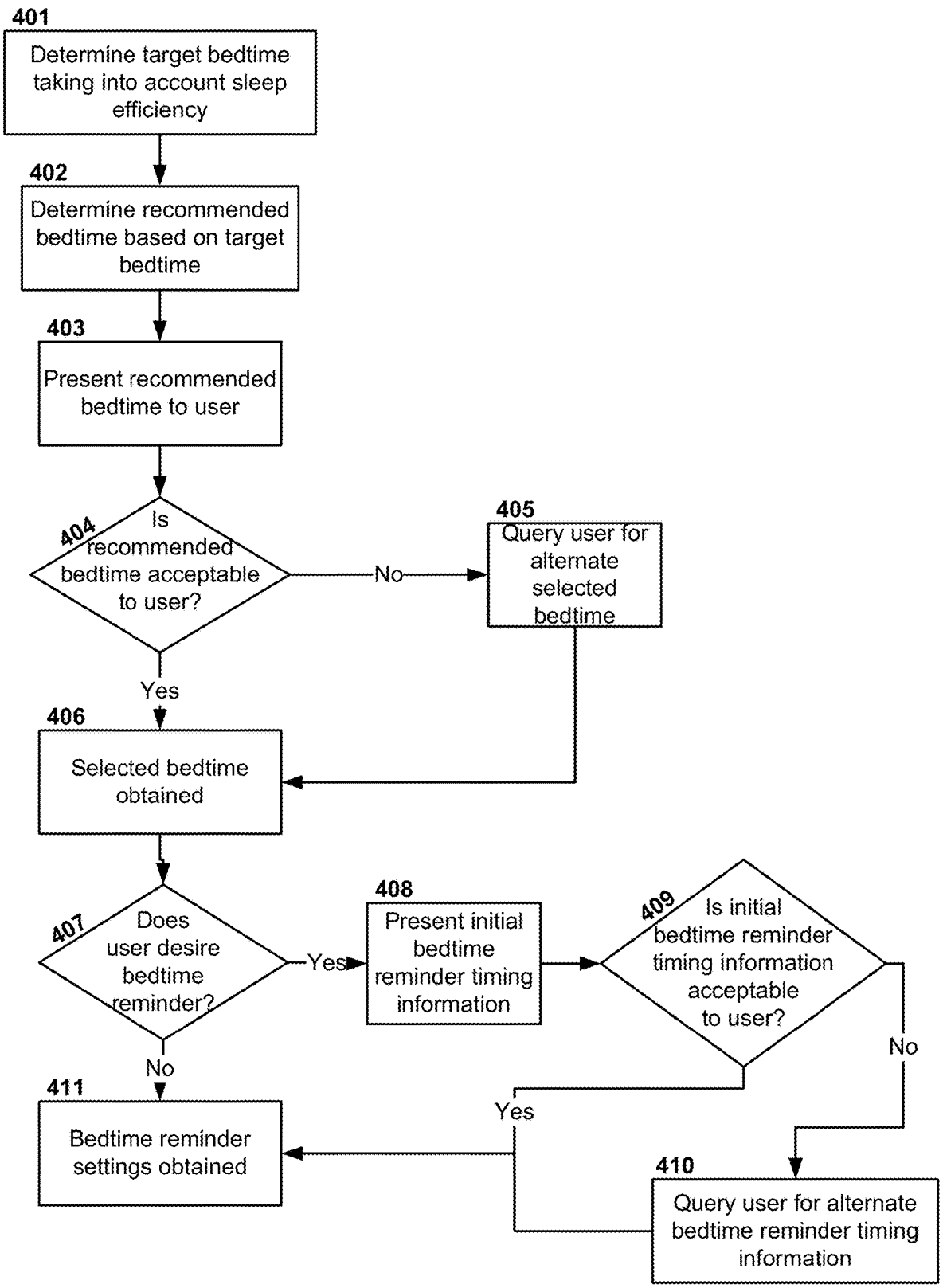
FIG. 4 depicts a high-level flow diagram of techniques for obtaining a selected bedtime.

Once a scheduled waketime and a selected sleep duration have been obtained, a selected bedtime may be obtained. FIG. 4 depicts a high-level flow diagram of techniques for obtaining a selected bedtime. To obtain a selected bedtime, a target bedtime may first be determined, taking into account the sleep efficiency of the individual (or of other individuals), in block 401; such a determination may also be based on the selected sleep duration and the scheduled waketime. Once the target bedtime has been determined, a recommended bedtime may be optionally determined in block 402 based on the target bedtime, as discussed in more detail below—the recommended bedtime may, for example, be modified from the target bedtime to be the closest 15-minute time on the hour to the target bedtime (in other implementations, the target bedtime may simply be used as the recommended bedtime). Once determined, the recommended bedtime may be presented to the individual in block 403 and the individual may be requested to confirm if the recommended bedtime is acceptable to the individual as a selected bedtime in block 404. If the individual indicates in block 404 that the recommended bedtime is acceptable, then the recommended bedtime may be used as the selected bedtime in block 406. If the individual indicates in block 404 that the recommended bedtime is not acceptable as the selected bedtime, then the individual may be prompted in block 405 to provide an alternate selected bedtime in block 405, which may then be used as the selected bedtime in block 406.

After a selected bedtime has been determined, the individual may be optionally presented with an opportunity to set a bedtime reminder in block 407. If the individual indicates in block 408 that no bedtime reminder is desired, then the bedtime reminder settings may be considered to have been obtained (with no reminder set) in block 412. If the individual indicates in block 407 that a bedtime reminder is desired, then initial bedtime reminder timing information may be presented to the individual in block 408, after which the individual may be presented in block 409 with an opportunity to indicate whether the initial bedtime reminder timing information is acceptable. If so, then the technique may proceed to block 411 using the initial bedtime reminder timing information as the bedtime reminder setting. If not, then the technique may first query the individual to enter alternate bedtime reminder timing information in block 410 before proceeding to block 412.

The techniques outlined above may be implemented in a variety of ways; the following discussion examines some of these implementations in the context of some example graphical user interfaces (GUIs). It is to be understood that GUIs may include a multitude of different graphical user interface elements, e.g., fields, controls, images, charts, graphs, buttons, sliders, etc. that may be used to convey or receive data to or from a user. While discrete GUIs are discussed below, such discrete GUIs may also be provided by simply replacing or updating a GUI element in one GUI to provide the information conveyed in another GUI (for example, the GUIs of FIGS. 12 and 13, which are discussed later, may be the same GUI with the same GUI elements, but with different data placed in two fields—"Adults are recommended to get 7-9 hours but everyone is different. For now, let's set your sleep goal to" is replaced by "Adults are recommended to get 7-9 hours. For now, let's set your sleep goal to," and "6 hr 30 min" is replaced by "7 hr 00 min"). Thus, in the discussions below, it is to be understood that reference to providing or generating a GUI is inclusive of causing a GUI element of a GUI to act in a particular way or display particular data or information that is to be conveyed via that GUI.

Computational Environment

The techniques and methods discussed herein are implementable in a variety of different computational environments involving a variety of computing platforms and may make use of a number of different computing systems. It is to be understood that the techniques and methods discussed herein are not to be limited to a particular computational environment, but may be implemented in a number of different specific ways consistent with this disclosure, and that all of these different implementations are within the scope of this disclosure.

Figure 5:
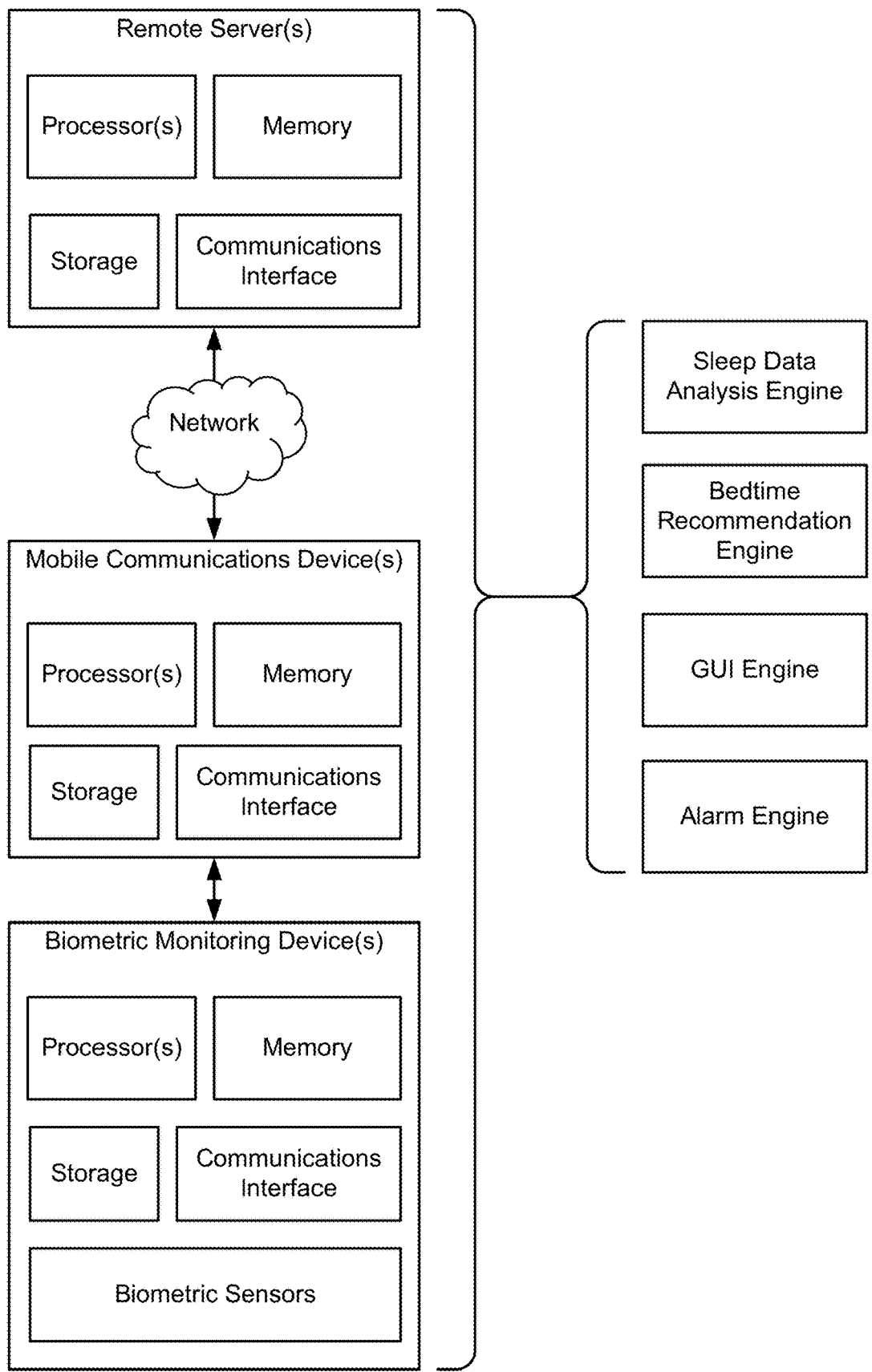
FIG. 5 is a block diagram of an example computational environment that may be used to implement the techniques and methods discussed herein.

FIG. 5 depicts a block diagram of an example computational environment that may be used to practice the techniques and methods discussed herein. As can be seen, the computational environment may include a remote server or servers, e.g., a cloud-based computing system, that may include one or more processors, memory (such as random-access memory that may be used to store computer-executable instructions during program execution and for temporary data storage), storage (such as hard disk arrays or other non-volatile storage media), and a communications interface (such as a TCP/IP network connection or similar communications interface). Such remote servers may be communicatively connected with a plurality of mobile communications devices, e.g., smartphones, tablets, etc., that may be owned and/or used by individuals owning and/or using biometric monitoring devices. The mobile communications devices may each similarly have one or more processors, memory, storage, and communications interfaces that allow them to communicate with the remote servers via a network. The communications interfaces of the mobile communications devices may also include a communications interface for communicating with the biometric monitoring devices, e.g., a Bluetooth communications interface or similar short-range, low-power link. The biometric monitoring devices may also have their own processors, memory, storage, and communications interfaces, as well as one or more biometric sensors that may be used to monitor activities of their users.

These various components or elements of the example computational environment may be configured to individually or cooperatively perform the various techniques and methods discussed herein. For example, the mobile communications device(s) may serve as an information relay between the remote server(s) and the biometric monitoring device(s), and may also serve to provide the GUIs discussed herein using, for example, a GUI engine that includes logic or computer-executable instructions for controlling the one or more processors of the mobile communications device to provide the various GUIs discussed herein. The biometric monitoring device(s) may, for example, collect data from the biometric sensors, store such collected data locally in the biometric monitoring device(s), and then upload the collected data to the remote server via the mobile communications device(s). The biometric monitoring device or the mobile communications device may also provide alarm functionality, e.g., the waketime and/or bedtime reminder alarms discussed later herein, via an alarm engine that includes logic or computer-executable instructions for controlling the one or more processors of such elements to provide such alarms. The remote servers, for example, may provide long-term storage of collected sleep data, as well as performing sleep data analysis, such as identifying periods spent in each sleep state, the timing of any waking events, etc., such as may be performed by a sleep data analysis engine. Such sleep data analysis may alternatively or additionally be performed by the mobile communications device and/or the biometric monitoring device, depending on the particular architecture that is implemented. A bedtime recommendation, as discussed later herein, may also be provided by a bedtime recommendation engine, which may include computer-executable instructions or logic for controlling one or more of the processors of one or more of the elements discussed above to determine a bedtime recommendation according to the techniques discussed herein.

The particular example depicted in FIG. 5 is only one representative example of a system and computational environment that may be used to implement the techniques and methods discussed herein, and it is to be understood that other systems and computational environments that may provide one or more aspects of the methods and techniques discussed herein are also considered within the scope of this disclosure.

Sleep Data Collection and Storage

As noted earlier, sleep data that is derived from sensor data that is generated by a biometric monitoring device may be used to evaluate how well the user is adhering to their desired sleep duration, as well as to provide further tools that may assist the user in attaining their desired sleep duration. The sleep data may include data for a plurality of sleep sessions and may specify various sleep states of the user for the respective sleep sessions, as well as bedtimes, and/or waketimes of the user for each respective sleep session. As stated above, the various sleep states of the user may also include or be representative of one or more various sleep stages of the user.

Figure 6:
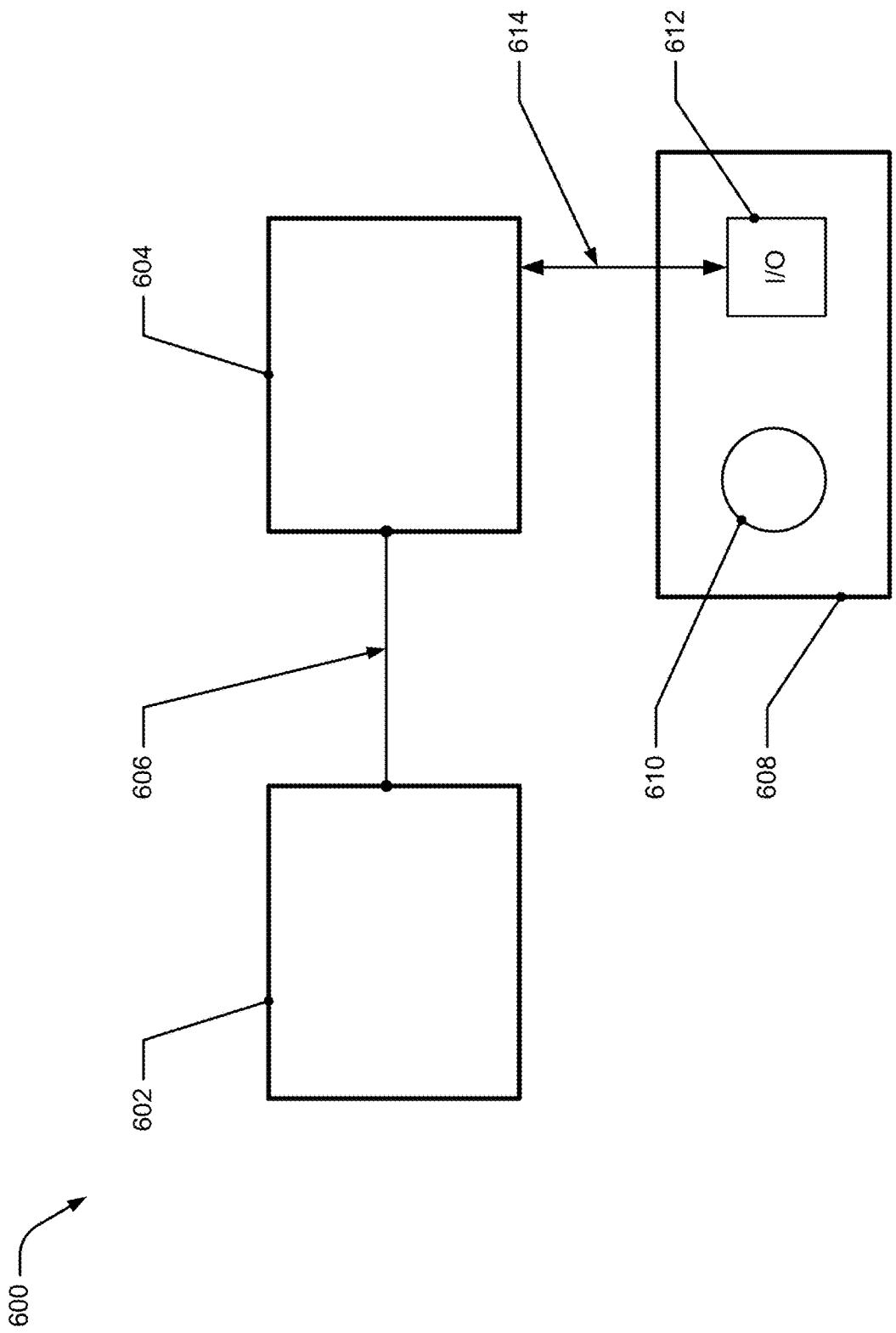
FIG. 6 depicts a high-level schematic of a sleep tracking system.

Sleep monitoring and/or tracking may also include storing the sleep data in a sleep log data store as one or more sleep logs associated with an account assigned to or associated with the user as well as sleep logs that include sleep data of other users of other biometric monitoring devices. The sleep log data store may be located in one or more memories of one or more databases that may be communicatively connected with each other as well as with the biometric monitoring device of the user and with biometric monitoring devices of the other users, whether directly or indirectly. For example, a biometric monitoring device may include a Bluetooth communications interface that may allow the biometric monitoring device to connect with a user's smartphone, which may, in turn, have a network communications interface that allows the smartphone to wirelessly connect with a remote server or servers, such as a cloud-based data storage system that may store the sleep log data store. The smartphone may thus act to relay information from the biometric monitoring device to the sleep log data store. FIG. 6 depicts an example system for implementing such sleep monitoring and/or tracking. As shown, the example system 600 includes a memory 602 and a processor 604 that are communicatively connected with each other, as indicated by line 606.

In some embodiments, the system may include a biometric monitoring device 608 that includes one or more sensors 610 and a communications interface 612 to communicate with the one or more processors 604 as indicated by line 614. The communications interface may use any known hard-wired, wireless, or other communication technique. The one or more sensors 610 may be configured to generate biometric sensor data that may be used to generate sleep data. In some embodiments, the sensor 610 of the biometric monitoring device 608 may generate sensor data and the memory 602 may contain instructions for controlling the processor 604 to obtain sleep data that is derived from the sensor data. In some such embodiments, the processor 604 may be part of the biometric monitoring device 608, on the user's computing device (e.g., a computer or a smart phone), and/or on one or more computing devices that are separate from the biometric monitoring device 608.

It is to be understood that, in actual practice, the processing and storage functionality discussed herein may be distributed among a number of different devices, rather than a single processor 604 and a single memory 602. For example, a biometric monitoring device may have one or more processors and a memory that are communicatively connected with one another and with one or more sensors of the biometric monitoring device. The memory of the biometric monitoring device may store computer-executable instructions for controlling the one or more processors of the biometric monitoring device to obtain sensor data from the one or more sensors. In some implementations, the memory of the biometric monitoring device may also store computer-executable instructions for controlling the one or more processors of the biometric monitoring device to analyze such collected sensor data to determine one or more biometric measurements, e.g., heart rate, steps taken, sleep state or stage, etc., as well as to communicate collected sensor data and/or determined biometric measurement data to a remote device, such as to a smartphone that may be communicatively connected with the biometric monitoring device (e.g., via Bluetooth connection) and/or a server, such as a cloud-based server. The remote device, which may have its own one or more processors and one or more memories, may store data provided by the biometric monitoring device in the one or more memories of the remote device, and may, in some implementations, perform further analysis on such data in order to determine additional biometric measurements or to refine previously-determined biometric measurements. For example, a biometric monitoring device may determine some biometric measurements using simplified computational methods that, while less accurate, may consume far less battery power than more involved computational methods. If the sensor data used to determine such biometric measurements is later transmitted to a remote device, e.g., to a server, the sensor data may be re-analyzed by the one or more processors of the remote device using more computationally-intensive techniques that provide a more accurate determination of that same biometric measurement. Thus, it is to be understood that the determination and storage of sleep data may be performed in any of a number of different devices and/or locations, and the techniques discussed herein are not to be viewed as being limited to implementation on only one type of device or system.

As discussed above, sleep data may be stored in a sleep log data store, which may be a data structure that stores sleep data and associates such sleep data with particular sleep sessions. There may be multiple instances of a sleep log data store. For example, a biometric monitoring device may store several days' worth of sleep sessions and sleep data, and a smartphone that is communicatively connected with the biometric monitoring device may store several weeks' or months' worth of sleep log data, and a remote device, e.g., a cloud-based storage system, may store months or years of sleep log data (or even store such data indefinitely).

It is also to be understood that the techniques discussed herein may involve calculations and/or determinations that may be made by processors located in a variety of different locations. For example, in some implementations, a target bedtime determination (discussed later herein) may be made by a processor or processors of a wearable biometric monitoring device using data stored on the biometric monitoring device. In other implementations, such a target bedtime determination may be made by a processor or processors of a mobile communications device, e.g., a smartphone, that is paired with the wearable biometric monitoring device. In yet other implementations, such a target bedtime determination may be made by a processor or processors of a remote device, such as a cloud server system, and the target bedtime determination (or a recommended bedtime determination based thereupon, also discussed later herein) may be sent to a mobile communications device, e.g., a smartphone, afterwards to allow such information to be provided to the user via a GUI of the mobile communications device.

New User/User New to Sleep Tracking—Initial Selected Sleep Duration Setup

As discussed earlier, in some implementations, a selected sleep duration may be obtained for a new user. Various further details of how such selected sleep durations may be obtained are discussed in more detail below, along with graphical user interfaces that may be used to assist in obtaining such selected sleep durations.

Figure 7:
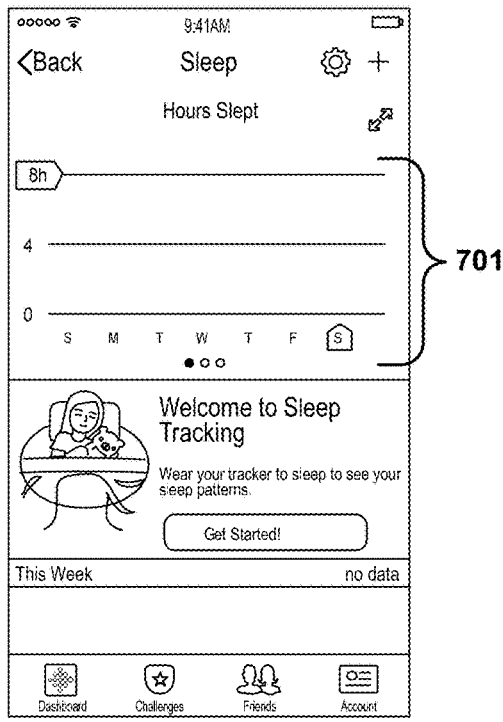
FIG. 7 is an example graphical user interface for a user new to sleep tracking.
Figure 8:
FIG. 8 is another example graphical user interface for a user new to sleep tracking.
Figure 9:
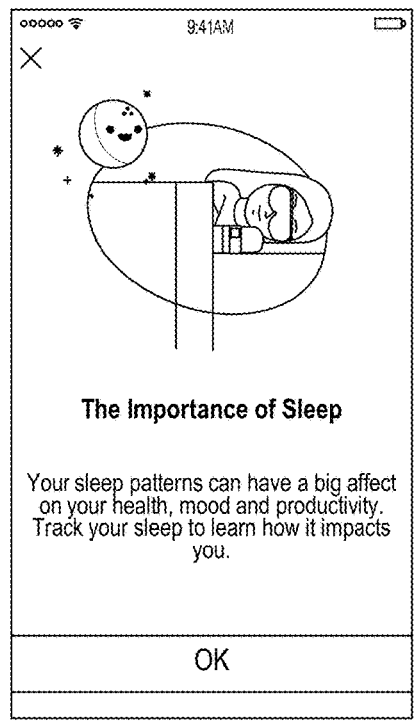
FIG. 9 is an example of a graphical user interface that may be generated for a user new to sleep tracking.

FIGS. 7 and 8 depict examples of two different graphical user interfaces that may be generated for a new user (each represents a different option for introducing the new user to sleep tracking). As can be seen, such graphical user interfaces (referred hereinafter as a "GUI" or "GUIs") may include placeholders 701 for information such as historical sleep data of the user, as well as a welcome message—such historical sleep data may be collected by the biometric monitoring device even if the user has not previously used or otherwise enabled the sleep tracking functionality of the biometric monitoring device before, although in this case, there is no historical sleep data, so "no data" is displayed (in the GUI of FIG. 8) and there are no indications of actual hours slept. These GUIs may also include a "Get Started" prompt which may obtain input from the user to setup sleep tracking for the user. As used herein, a "prompt" may receive information and/or input from a user. Further, also as used herein, any time a user is described as inputting any data or information into a GUI, including selecting a prompt in a GUI, it may be considered that a processor providing such a GUI or otherwise linked or associated with the GUI, e.g., a processor at a remote server that is provided such data or information by, for example, accessing such data from a memory where it has been stored, obtains such data, information, and/or selection. Such setup for sleep tracking may include the generation of additional GUIs to obtain sleep-related information from the user and to display sleep-related information, as will be described in more detail below. FIG. 9 depicts another GUI that may be generated for a new user or a user being introduced to sleep tracking. If the user responds to the prompt to "Get Started" with sleep tracking, the new user may, in some implementations, be introduced to the concept and importance of sleep tracking, e.g., by one or more follow-on GUIs such as the GUI of FIG. 9. The GUI of FIG. 9 may include sleep-related information, such as information regarding the importance of sleep, as well as a prompt, e.g., "OK", which may be selected in order to transition to another GUI, such as the GUI of FIG. 10. The GUI of FIG. 9 may be generated before or after FIGS. 7 and 8 or may, in some cases, be omitted entirely.

Figure 10:
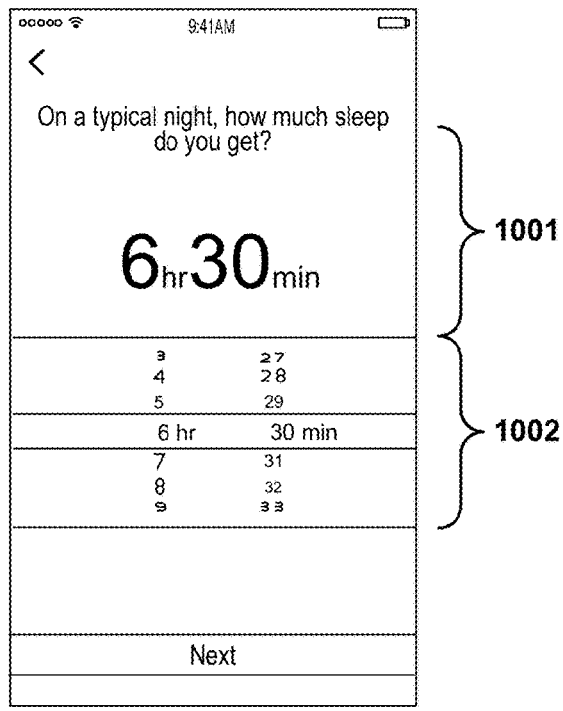
FIG. 10 is an example of a graphical user interface that may be generated in order to allow a user to provide the amount of sleep that they believe they typically attain each night.

FIG. 10 depicts a GUI that may be generated as part of a technique for obtaining a selected sleep duration of the user.

As used herein, "selected sleep duration" is used synonymously with "sleep goal," and represents the amount of actual sleep (as may be estimated by a biometric monitoring device) that the user would like to achieve during a sleep session or sleep sessions. As can be seen, the GUI of FIG. 10 includes a prompt 1002 that can be user-adjusted to specify an amount of sleep 1001 that the user believes he or she gets during a typical sleep session, such as typical night's sleep. In some implementations, the amount of sleep entered into the prompt may be used as a starting point for obtaining a selected sleep duration via additional GUIs, as is discussed further below. In other implementations, the amount of sleep input by the user to the GUI, i.e., obtained by the GUI of FIG. 10, may be considered the selected sleep duration (or sleep goal) of the user which may be used in other aspects of sleep tracking as discussed below. In this later implementation, the call of the GUI shown in FIG. 10 may specify "Please set an amount of sleep you would like to get" or some variant thereof.

Figure 11:
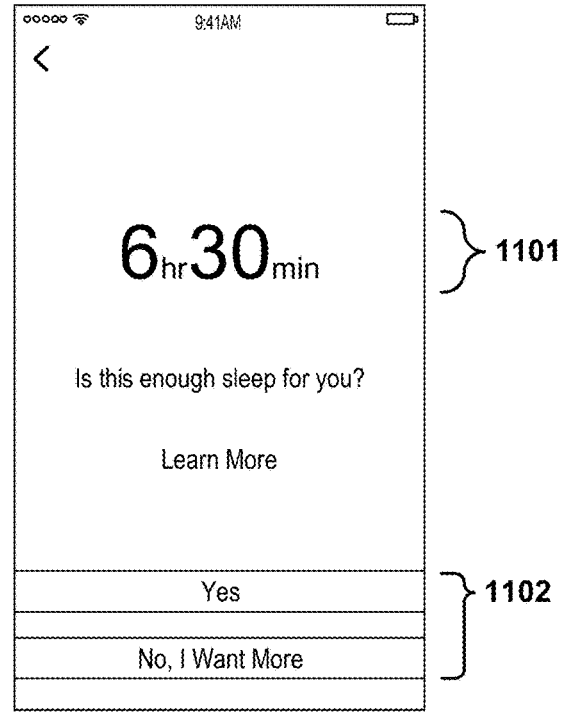
FIG. 11 is an example of a graphical user interface that may be used to confirm whether a selected sleep duration for a user is sufficient.

In some implementations, another GUI may be generated after the amount of sleep is input to the GUI of FIG. 10. For instance, FIG. 11 depicts a graphical user interface that may be generated after FIG. 10. As can be seen, the GUI of FIG. 11 may include, e.g., display, the amount of sleep 1101 obtained by the GUI of FIG. 10 and may provide a prompt 1102 to allow the user to confirm that the typical amount of sleep input by the user is enough sleep or to indicate that the user would like to get more sleep. The GUI may obtain inputs from the user when the user selects the "Yes" or "No, I Want More" prompts (or similar prompts) which may be included in the GUI.

Figure 12:
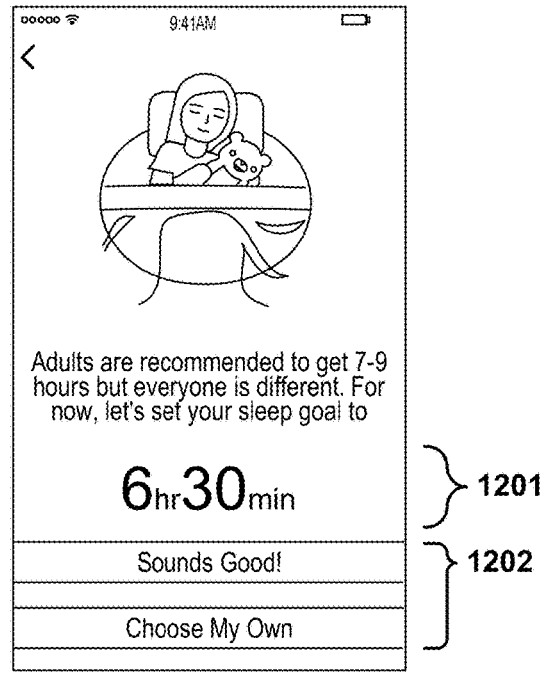
FIG. 12 is an example of a graphical user interface that may be presented to a user if the user selects a selected sleep duration that is less than a recommended amount of sleep duration.

In some such implementations, if the user inputs in a GUI, such as the GUI of FIG. 11, that the amount of sleep is sufficient, then another GUI may be generated, such as FIG. 12, which depicts a GUI that may be generated after FIG. 11. Here, as with the GUI of FIG. 11, the GUI of FIG. 12 may include the amount of sleep 1201 obtained in FIG. 10 as well as information related to the amount of sleep obtained in FIG. 10. For example, if the amount of sleep obtained in FIG. 10 is outside a range of predetermined sleep durations, then information may be included in the GUI that is intended to educate the user about recommended sleep and/or encourage the user to change the selected sleep duration to a value within the range of predetermined sleep durations. For instance, in FIG. 12, the information included in the GUI informs the user that the selected sleep duration of 6 hours and 30 minutes is outside a recommended sleep duration range of 7-9 hours for adults. However, the GUI of FIG. 12 also acknowledges that every person is different, thereby gently educating the user as to the recommended sleep duration.

Figure 13:
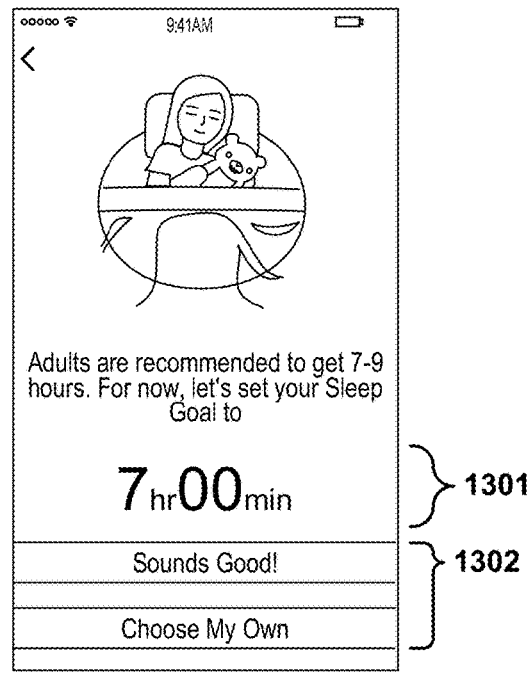
FIG. 13 is an example of a graphical user interface that may be presented to a user if the user previously indicated that they would like to increase their selected sleep duration.

If the user inputs that more sleep is desired in the prompt 1202 of the GUI of FIG. 10, then the GUI of FIG. 13 may be generated. The GUI of FIG. 13 includes sleep-related information that may be displayed to the user, similar to that displayed in FIG. 12, which here is information that informs the user about recommended sleep durations for adults; since the user has already indicated dissatisfaction with their typical sleep duration (by way of selecting the "No, I Want More" prompt), the information regarding the typical sleep durations of adults may be presented in a more emphatic manner than in the GUI of FIG. 12, e.g., the phrase "but everyone is different" may be omitted. The GUI of FIG. 13 also includes a recommended sleep duration 1301 which may be determined in any number of various ways, such as are described in detail below. In some embodiments, the recommended sleep duration may be calculated based, at least in part, on past or historical user-selected sleep duration; sleep data, including the selected sleep duration, of other users of sleep tracking and/or biometric monitoring devices; a look-up table; demographics of the user (e.g., age, weight, gender); a geographic location of the user; specific days of the week; a specific time of year; holidays; a seasonal time change; exercise of the user; duration of daylight; and/or general guidelines of sleep durations for users. For example, in FIG. 13, the system may set the recommended sleep duration to 7 hours and 00 minutes, which is the lowest sleep duration in the depicted range of recommended sleep durations for adults. Such recommended sleep duration may also be calculated by adding an incremental amount to the selected sleep duration specified in the prompt 1002 in FIG. 10, such as increment the selected sleep duration by 15 minutes or 30 minutes. The user may then indicate that they find the selected sleep duration acceptable or unacceptable via a prompt 1302.

The GUIs of both FIGS. 12 and 13 also include prompts which may obtain the user's selection of whether the recommended or selected sleep duration that is depicted is acceptable ("Sounds Good!") or whether the user would like to choose her own sleep duration ("Choose My Own"). If the user selects the "Sounds Good!" prompt, then the recommended sleep duration as shown on either of the GUIs shown in FIG. 12 or 13 may be stored as the selected sleep duration.

Figure 14:
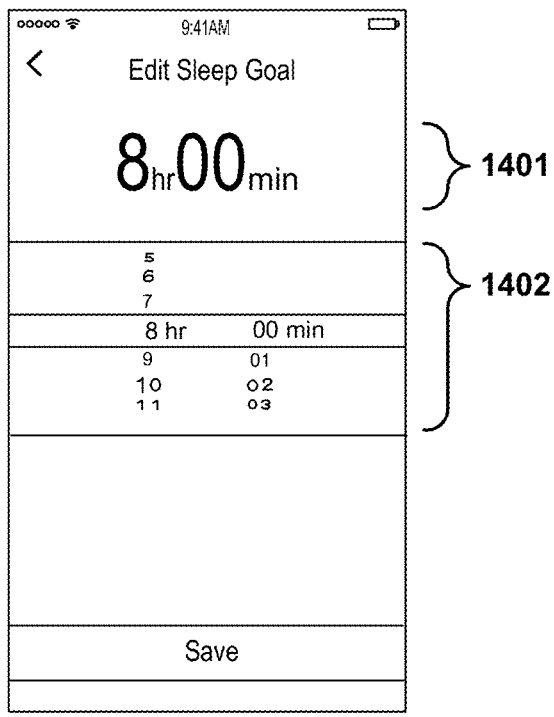
FIG. 14 is an example of a graphical user interface that may be presented to a user in order to allow the user to change their selected sleep duration.

If a GUI obtains the user's input to choose her own sleep duration, e.g., the user selects the "choose my own" prompt in either of the GUIs of FIG. 12 or 13, then another GUI may be generated. FIG. 14 depicts a graphical user interface that may be generated after 13 and, as can be seen, this GUI includes a selected sleep duration 1401 and a prompt 1402 to allow the user to change the selected sleep duration. This selected sleep duration may, like in FIG. 13, override any previously obtained selected sleep durations and become the selected sleep duration.

Once the selected sleep duration is obtained by the GUI, a memory communicatively connected with one or more processors may include instructions for controlling the one or more processors to store the selected sleep duration in the memory or in a sleep log data store such that the selected sleep duration is associated with an account assigned to or associated with the user, as discussed further below. The sleep log data store may, for example and as discussed earlier, be a database or other structured data construct that stores sleep logs associated with one or more user accounts (which are each associated with a particular user). A sleep log, for example, may be a record that is representative of sleep data from a user's sleep session, e.g., it may have data indicating the start and end of the sleep session, the amounts of time spent in various sleep states, the number of times the person woke up during the sleep session, etc. There may be multiple instances of sleep log data stores that may be utilized in the various implementations discussed herein—for example, a local sleep log data store may be maintained in the memory of a user's biometric monitoring device or smartphone and may be used to store sleep logs for that user. Alternatively, or additionally, an external server or servers, e.g., a cloud-based system, may provide a global sleep log data store that may be used to store sleep logs for that user as well as multiple other users; processors having access to either type of sleep log data store may be able to access sleep data from the sleep logs stored therein and to perform calculations utilizing such data.

Figure 15:
FIG. 15 is an example of a graphical user interface that may be used to provide instructions to a user of a wearable biometric tracking device with manually activated sleep tracking.

Instructing Users on how to Enable Sleep Tracking in a Biometric Monitoring Device After the user's selected sleep duration is obtained, in some implementations a GUI may be generated that includes information related to the user's biometric monitoring device, such as further instructions for how to use their biometric monitoring device to track sleep. In some embodiments, a determination may be made as to whether the biometric monitoring device of the user is a biometric monitoring device with automatic sleep tracking functionality or a biometric monitoring device with manually-triggered sleep tracking functionality. This may be determined, for example, by comparing the model of the biometric monitoring device against a list or lists of biometric monitoring devices having automatic sleep tracking or manual sleep tracking. For some biometric monitoring devices that may not be configured to automatically detect, track, and/or monitor the user's sleep, the GUI of FIG. 15 may be generated. FIG. 15 depicts a graphical user interface generated for biometric monitoring devices that do not include automatic sleep detection, tracking, and/or monitoring. As can be seen, the GUI of FIG. 15 includes information confirming that the selected sleep duration, i.e., sleep goal, has been set. As noted above, once the selected sleep duration is input, it may be stored in a memory and/or sleep log data store such that it is associated with the user. The GUI of FIG. 15 also includes instructional information about using the biometric monitoring device in order to monitor and track the user's sleep—in this case, the user is instructed to push and hold a button on the biometric monitoring device to mark the start and stop sleep tracking, e.g., the beginning and end of a sleep session. For some biometric monitoring devices that may be configured to automatically detect, track, and/or monitor the user's sleep, the GUI of FIG. 16 may be generated. Here, the GUI of FIG. 16 includes information confirming that the selected sleep duration, i.e., sleep goal, has been set, as well as instructional information about using the biometric monitoring device in order to monitor and track the user's sleep—in this case, the user need only wear the biometric monitoring device and the biometric monitoring device may automatically identify when the user is in a sleep session, so the user is only prompted to remember to wear the biometric monitoring device to bed. It will be appreciated that the particular GUI displayed, e.g., such as the GUIs of FIGS. 15 and 16, may be selected based on the determination as to whether or not the user's biometric monitoring device has automatic sleep tracking.

Figure 16:
FIG. 16 is an example of a graphical user interface that may be used to provide instructions to a user of a wearable biometric tracking device with automatic sleep tracking.
Figure 17:
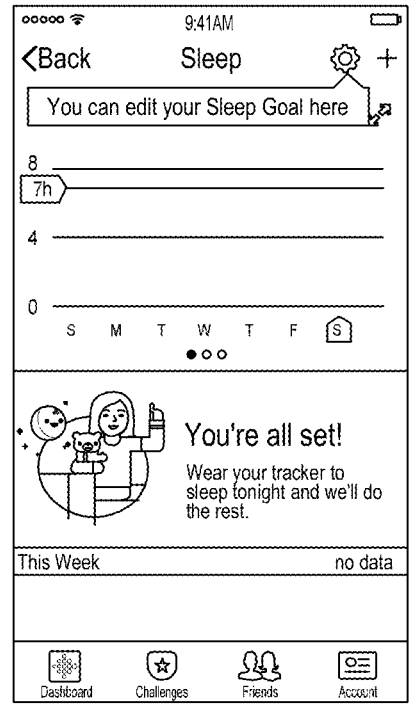
FIG. 17 is an example of a graphical user interface that may be used to provide instructions to a user once initial sleep tracking parameters have been established.
Figure 38:
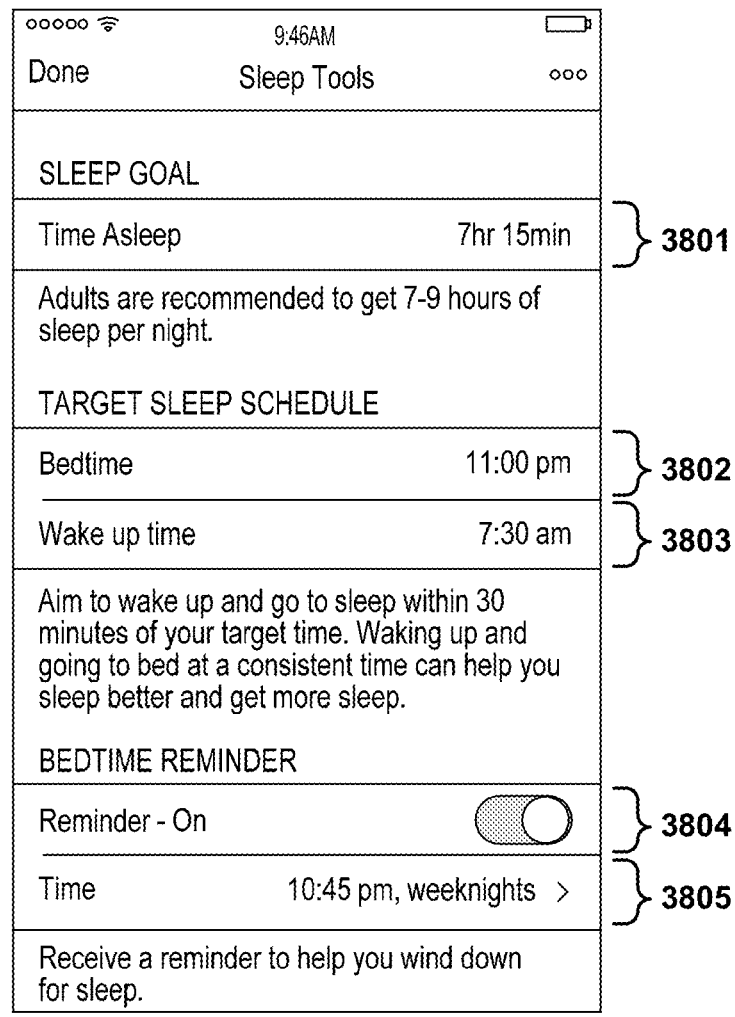
FIG. 38 is an example of a graphical user interface that may be used to allow a user to edit sleep scheduling parameters.

FIG. 17 depicts a graphical user interface that may be generated after FIG. 15 or 16. Here, the GUI may include information about making changes to the selected sleep duration, i.e., the sleep goal, as well as information related to sleep data of the user, such as sleep duration data, waketimes, and/or bedtimes. For example, the "You can edit your sleep goal here" callout may be used to indicate a user interface element that may allow a user to access, for example, a dashboard GUI such as is shown in FIG. 38, which is discussed later, which may allow the user to easily change various sleep scheduling parameters. For a new user, the GUI of FIG. 17 may include the capability to display sleep data, but there may not yet be enough (or any) sleep data generated and/or collected by the user's biometric monitoring device to display in the GUI of FIG. 17.

Establishing a Sleep Schedule—Potential Recalibration of Selected Sleep Duration FIGS. 18 and 19 depict graphical user interfaces that may be generated after some sleep data derived from sensor data generated by the biometric monitoring device have been obtained and stored in the sleep log data store. Such sleep data may indicate that the user is consistently unable to meet the selected sleep duration, and may the display of a GUI that allows for recalibration of the selected sleep duration to a selected sleep duration that is perhaps easier for the user to achieve. Such interfaces, or similar interfaces, may also be used during initial sleep duration setting if sleep data has already been obtained at the time that the initial selected sleep duration is set.

The GUIs in FIGS. 18 and 19 include the graphical representation of at least some sleep data of the user relating to actual time slept. For instance, each of the two GUIs include a graphical representation 1801 or 1901 of the "Hours Slept" of the user for particular days of a week as well as an average amount of the "Hours Slept" for the week. The "Hours Slept" information may be derived from the obtained and stored sleep data, and may be representative of various sleep states of the user, depending on what sleep states are considered to be "sleeping." As also seen in these Figures, the GUIs may include a prompt for the user to set a sleep schedule.

Figure 21:
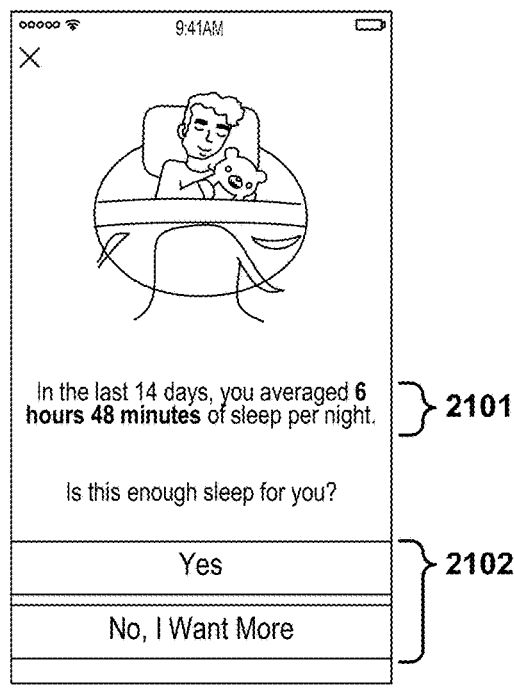
FIG. 21 is another example of a graphical user interface that may be used to present typical sleep duration of the user and inquire whether that amount of sleep duration is sufficient.

In some implementations of generating one or more personalized GUIs for setting the sleep schedule of the user of the biometric monitoring device, a GUI may be generated that is similar to the GUIs of FIGS. 11 through 13, except that instead of a user-supplied typical sleep duration, the GUI may provide a calculated typical sleep duration based on the actual sleep durations determined for one or more sleep sessions for which biometric sensor data has been obtained. FIGS. 20 and 21, for example, depict graphical user interfaces that may be used, at least in part, to obtain a selected sleep duration of the user after sleep data for some period of time has been obtained. As can be seen in FIGS. 20 and 21, the GUIs include information 2001 or 2101 related to and/or based, at least in part, on the sleep data of the user that has been collected. Such information may include sleep duration, e.g., average time spent in the various sleep states during some number of past sleep sessions and/or during a specific period of time, e.g., the past week or past two weeks. Here, the GUI of FIG. 20 includes an average amount of sleep for the user for the last five sleep sessions (i.e., "sleeps"), whereas the GUI of FIG. 21 includes an average amount of sleep for the user during the previous 14 day period. These GUIs may also include prompts 2002 or 2102 which may receive input from the user to either accept the presented sleep duration ("Yes") as the selected sleep duration, i.e., sleep goal, or to select a different selected sleep duration ("No, I Want More").

Figure 22:
FIG. 22 is an example of a graphical user interface that may be used to present a recommended sleep duration and allow a user to confirm or modify that recommended sleep duration.

FIG. 22 depicts a graphical user interface that may be generated to obtain an updated selected sleep duration. The GUI of FIG. 22 may be generated after FIG. 20 or 21 if the user input that the information displayed in the GUI of FIG. 20 or 21, e.g., average sleep duration of the user, is acceptable as the selected sleep duration. The GUI of FIG. 22 may also include a recommended sleep duration 2201 that is related to the information presented in the GUI of FIG. 20 or 21, such as a sleep duration within a particular amount of time to the information presented in the GUI of FIG. 20 or 21. For example, FIGS. 20 and 21 included actual measured average sleep durations and the GUI of FIG. 22 includes a recommended sleep duration that is not the same as these average sleep durations, but is within three minutes of these average sleep durations. In some embodiments, the recommended sleep duration may, for example, be rounded to the closest 15-minute increment to the average sleep duration presented in the GUI of FIGS. 20 and 21. In some other embodiments, the recommended sleep duration of the GUI in FIG. 22 may be the same as the sleep duration presented in FIG. 20 or 21.

Figure 23:
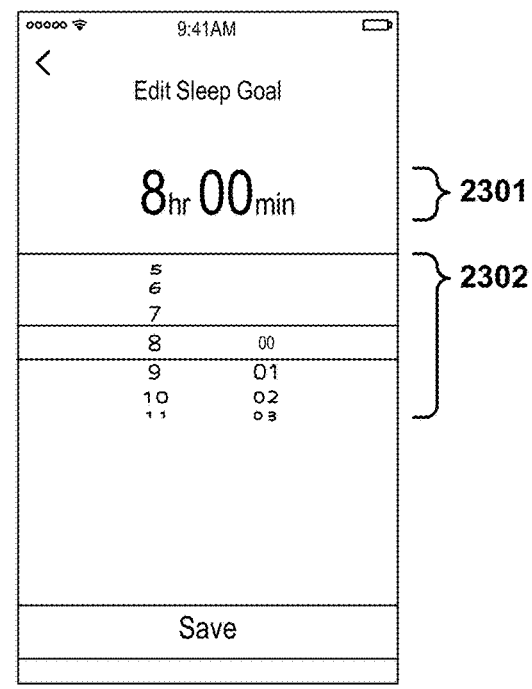
FIG. 23 is an example of a graphical user interface that may be used to allow the user to update a selected sleep duration.

Prompts 2202 are included in FIG. 22 for the user to either accept the recommended sleep duration as the selected sleep duration, i.e., sleep goal, or to choose a different selected sleep duration. If the user accepts the recommended sleep duration, then the recommended sleep duration is stored as the selected sleep duration of the user. If the user elects to choose a different selected sleep duration, then FIG. 23 may be generated. FIG. 23 depicts a graphical user interface that may be generated to, at least in part, obtain a user-specified selected sleep duration. FIG. 23 includes prompts to obtain an input sleep duration by the user which may be stored as the selected sleep duration.

Figure 24:
FIG. 24 is an example of a graphical user interface that may be used to present a recommended sleep duration to the user and to inquire whether that amount of sleep duration is sufficient.

FIG. 24 depicts a different graphical user interface that may be generated to obtain a selected sleep duration, for example, in response to the user selecting "no, I want more" in the GUI of FIG. 21. Here, the GUI may include a recommended sleep duration 2401 that is more than the sleep duration information included in the GUI of FIG. 20 or 21. As stated above, the GUIs of FIGS. 20 and 21 included average sleep durations of the user and here in FIG. 24, the recommended sleep duration is greater than those average sleep durations. The amount by which the recommended sleep duration is greater than the presented sleep duration may vary. In some implementations the amount may be 30 minutes from the sleep duration information previously presented to the user; for example, if the sleep duration information presented to the user, as in FIG. 21, is an average sleep duration of 6 hours and 48 minutes, then the recommended sleep duration may be 7 hours and 18 minutes. In some implementations, the amount may be 30 minutes from the nearest 15-minute increment of the presented sleep duration information; for instance, if the sleep duration information presented to the user, as in FIG. 21, is an average sleep duration of 6 hours and 48 minutes, then the closest 15 minute increment to that sleep duration is 6 hours and 45 minutes and therefore the recommended sleep duration may be 7 hours and 15 minutes, as depicted in FIG. 24.

Similar to FIG. 22, FIG. 24 includes prompts 2402 for the user to either accept the recommended sleep duration as the selected sleep duration or to choose a different selected sleep duration. If the user accepts the recommended sleep duration, then the recommended sleep duration may be stored as the selected sleep duration of the user. If the user elects to choose a different selected sleep duration, then FIG. 23 may be generated which includes prompts 2302 to obtain an input sleep duration 2301 by the user which may be stored as the selected sleep duration.

Figure 25:
FIG. 25 is an example of a graphical user interface that may be used to introduce a user to the concept of a sleep schedule.

FIG. 25 depicts a graphical user interface that may be generated after a selected sleep duration has been selected by the user. This GUI may be generated after, for instance, the selection of the selected sleep duration in FIGS. 22 through 23. This GUI may serve as an introduction to setting up a sleep schedule.

Establishing a Sleep Schedule—Establishing a Scheduled Waketime

Figure 26:
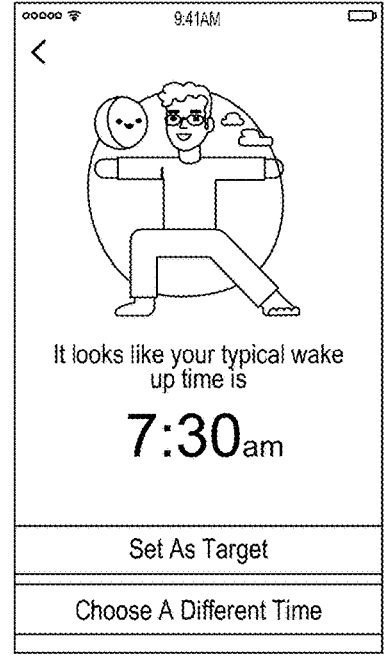
FIG. 26 is an example of a graphical user interface that may be used to present the user's typical waketime to the user and to inquire whether that waketime is acceptable as a scheduled waketime.

In some implementations of generating one or more personalized GUIs for setting the sleep schedule of the user of the biometric monitoring device, the generation may include generating one or more GUIs to obtain the scheduled waketime of the user. FIG. 26 depicts a graphical user interface that may be generated, at least in part, to obtain the scheduled waketime of the user. The GUI of FIG. 26 may include information 2601 related to and/or based, at least in part, on the sleep data of the user, which may include past waketimes of the user. Such past waketimes may be an average waketime for a specific period of time, such as two weeks; an average waketime for a specific number of sleep sessions; a single past waketime of the user; or another metric of past waketimes of the user. This information may, in some embodiments, be considered a recommended waketime. Such a past waketime may, for example, be rounded to the nearest 15-minute interval on-the-hour to make it easier for the user to interpret.

FIG. 26 may also include prompts 2602 for the user to accept the displayed information (e.g., an average waketime) as the target or scheduled waketime. In some such embodiments, as discussed above, this information may be a recommended waketime which the user may accept by selecting one prompt of FIG. 26 (e.g., "Set As Target") or may change by selecting another prompt of FIG. 26 (e.g., "Choose A Different Time"). If the user selected the recommended waketime as the scheduled waketime, then the recommended waketime is stored as the scheduled waketime. The scheduled waketime may be used to set an alarm to wake the user up at the scheduled waketime, but, more importantly, the scheduled waketime may be used in determining a recommended bedtime for the user based on their selected sleep duration.

Figure 27:
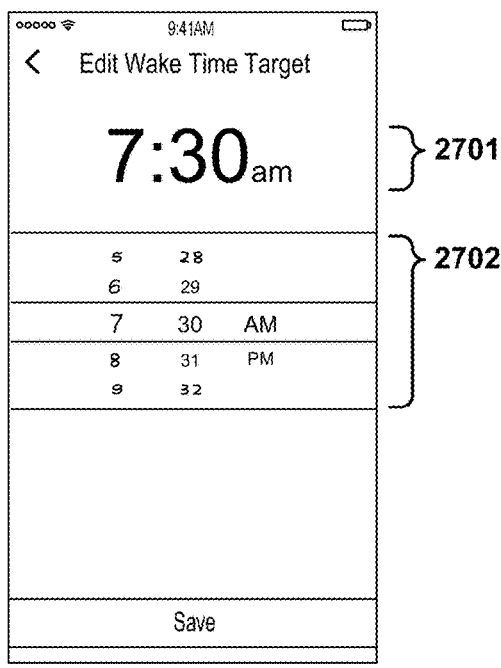
FIG. 27 is an example of a graphical user interface that may be used to allow the user to adjust their scheduled waketime.

FIG. 27 depicts a different graphical user interface that may be generated, at least in part, to obtain the scheduled waketime of the user. The GUI of FIG. 27 may be generated if the user selects to choose a different waketime in the GUI of FIG. 26. Here, the user may be provided with a prompt 2702 to allow the user to input any waketime 2701 which will be received by the GUI and stored as the scheduled waketime of the user.

Establishing a Sleep Schedule—Setting Waketime Alarms

Figure 28:
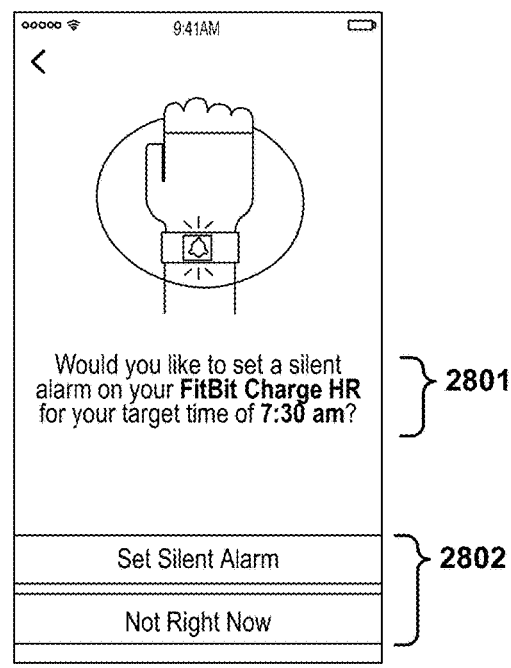
FIG. 28 is an example of a graphical user interface that may be used to allow the user to indicate whether or not an alarm should be set to wake the user up at the scheduled waketime.

FIG. 28 depicts a graphical user interface generated to obtain user preferences regarding a waketime alarm. The GUI of FIG. 28 may, for example, provide an indication 2801 of when the waketime alarm would be set for, as well as prompts 2802 to allow the user to enable or disable the waketime alarm. The GUI of FIG. 28 may alternatively or additionally obtain timing and/or day information regarding the waketime alarm such as a time, a date, and/or a specific day for which the waketime is alarm is to be activated. In some embodiments, the GUI of FIG. 28, or another GUI, may obtain a selected notification for the scheduled waketime alarm; the user may select the mechanisms in which the waketime alarm will occur, such as an auditory output, an electronic communication, an electromagnetic communication, a visual output (such as very bright light that may simulate daylight), and/or a tactile output that is described in greater detail below. In some such implementations, the biometric monitoring device may include a notification mechanism that is configured to provide such notifications; alternatively, such a notification may be generated by a smartphone that is paired with the biometric monitoring device.

Establishing a Sleep Schedule—Establishing a Selected Bedtime

In some embodiments, once the user's selected sleep duration, i.e., sleep goal, has been obtained and stored, the user's sleep may be tracked for a specified or predetermined period of time and/or number of sleep sessions before the generation of additional personalized GUIs, including a GUI based on the calculation of a specifically tailored target bedtime for the user, as is described in more detail in a later section. These additional GUIs may be used to assist the user with modifying their behavior so as to better achieve their selected sleep duration. As most people have little flexibility in the time they wake up, e.g., they must get up at a certain time in order to arrive at work or school at a scheduled time, such GUIs may generally be designed to promote the selection of a recommended bedtime that will allow the user to reliably achieve their desired sleep duration—a user typically has much more control over their bedtime, so helping the user establish and adhere to an appropriate bedtime may be the most effective technique for promoting regular sleep patterns.

In some implementations, a recommended bedtime may only be provided after a minimum amount of sleep data for the user is acquired. For instance, the minimum amount of sleep data may be sleep data gathered over a certain period of weeks, such as three weeks; it may be sleep data gathered for a certain number of sleep sessions, such as five; or it may be a combination in which the minimum is sleep data gathered for a certain number of sleep sessions over a certain period of time, such as five sleep sessions over two weeks. In some embodiments, once the minimum amount of sleep data is obtained, additional personalized GUIs may be generated based on at least that minimum amount of sleep data. In other implementations, the collection of sleep data of the user before generating the additional personalized GUIs for recommending a bedtime may be skipped, and the recommended bedtime may be determined according to other techniques, as discussed in more detail later.

In some implementations of generating one or more personalized GUIs for setting the sleep schedule of the user of the biometric monitoring device, the generation may include calculating a target bedtime based, at least in part, on the scheduled waketime and a sleep efficiency based on the sleep data for one or more users stored in the sleep log data store. The target bedtime may be calculated in order to provide the user with a recommended bedtime that increases the likelihood of consistent and healthy sleep. The target bedtime may also be calculated in order to provide the user with the recommended bedtime that will most likely result in the selected sleep duration, e.g., sleep goal, based on the scheduled waketime.

Sleep efficiency, as used herein, refers to the total time in a sleep session that an individual is in one or more sleep states that is or are not an awake state, divided by the sleep session duration, or a similarly equivalent measure of sleep efficiency. For example, the individual may get into bed at 11:00 p.m., take 30 minutes to fall asleep, wake up periodically during the night for a total of 30 minutes, and then wake up at 7:00 a.m. Here, the individual was attempting to sleep for a total of 8 hours (11:00 p.m.-7:00 a.m.), but was actually in the non-awake sleep state for 7 hours (8 hours in bed less 30 minutes to fall asleep and less 30 minutes in an awake sleep state during the night). The individual's sleep efficiency for this example night is 7 hours divided by 8 hours, or 0.875. Each user will have a different average sleep efficiency based on their physiology, sleep environment, etc. Sleep efficiency may also change night-to-night due to various factors such as whether or not the user consumed alcohol and/or caffeine, was traveling, is sick, etc. Sleep efficiency may also change depending on when a person goes to bed—for example, if a person goes to bed too early, they will likely be less tired and it will be harder for them to fall asleep quickly. If the person goes to bed later, they will be more tired and spend less time falling asleep, thereby likely increasing the amount of time that is spent sleeping in that sleep session.

It is to be understood that sleep efficiency may be evaluated based on how much total time a person spends in one or more designated sleep states during a sleep session divided by the sleep session duration. In some implementations, the designated sleep states may include all non-awake sleep states, in which case the sleep efficiency may be the total time in a sleep session spent asleep (regardless of how restless the person is while sleeping) divided by the sleep session duration. This is perhaps the simplest type of sleep efficiency to determine. In other implementations, however, sleep efficiency may be more nuanced, e.g., the designated sleep states may only include a non-empty subset of the non-awake sleep states, such as the sleep states that are known to be most restful and recuperative for the human body. In such an implementation, the sleep efficiency may be much lower than in the total-time-asleep example discussed previously. The selection of which sleep states to include in the determination of sleep efficiency may be pre-set or may be selectable by the user.

Because sleep efficiency is typically less than 1 (while it is never more than 1, it can, theoretically, be equal to 1 if a person immediately falls asleep when going to bed and otherwise spends the entire sleep session in the desired sleep states), recommending a bedtime by simply subtracting the selected sleep duration from the scheduled waketime does not result in an effective recommended bedtime. For example, if the user wants to wake up at 7:00 a.m. and get 8 hours of sleep, then subtracting 8 hours from 7:00 a.m. to reach a recommended bedtime of 11:00 p.m. (which is exactly 8 hours before 7:00 a.m.), will generally result in the user not receiving the full 8 hours in the various desired non-awake sleep states. As discussed herein, the sleep efficiency and various other factors may be used to calculate a more accurate, personalized, recommended bedtime for the user that will tend to cause the user to achieve the selected sleep duration.

As stated above, the system depicted in FIG. 6 may be used to implement such calculations of the target bedtime. Similar to above, the memory, which is communicatively connected with the one or more processors, may store instructions for controlling the one or more processors to obtain sleep data derived from sensor data generated by the biometric monitoring device, the sleep data including a plurality of sleep sessions that each specify various sleep states of the user for the respective sleep sessions, and to store the sleep data in the sleep log data store as one or more sleep logs associated with an account assigned to the user. In some implementations, the sleep log data store may also include sleep logs including sleep data derived from sensor data generated by other biometric monitoring devices of other users. The memory may also store instructions to calculate the target bedtime based, at least in part, on the scheduled waketime of the user and the sleep efficiency that is based on the sleep data for one or more users stored in the sleep log data store.

In some implementations, the recommended bedtime may be based, at least in part, on the sleep efficiency of the user of the biometric monitoring device. In some other implementations, the recommended bedtime may be based, at least in part, on the sleep efficiency of other users of other biometric monitoring devices; these other users may be filtered and selected in any number of various ways, which is discussed below.

The sleep efficiency may thus be representative, at least in part, of a correlation between sleep state duration data for one or more sleep sessions and sleep session duration data for those respective one or more sleep sessions. The memory may store instructions for controlling the one or more processors to obtain sleep state duration data for a sleep session stored in the sleep log data store and to determine sleep session duration data for a sleep session stored in the sleep log data store; the sleep state duration data and sleep session duration data may both be based, at least in part, on the sleep data derived from the sensor data generated by the biometric monitoring device. The sleep state duration data, as mentioned above, may be representative of the total amount of time the user that is associated with the sleep session spent in a designated subset of sleep states during the sleep session. The subset of sleep states may include non-awake sleep states, but does not include awake sleep states. While most sleep data may be obtained directly from sensor measurements, some sleep data, e.g., the start and end of a sleep session, may potentially be obtained from user input, e.g., when a user pushes a button on a biometric monitoring device to mark the start and/or end of a sleep session.

The sleep efficiency that is calculated for a person may be used to better predict how long of a sleep session that person will require in order to achieve the selected sleep duration for that person, which may, in turn, drive the determination of a target bedtime for that person. For example, the sleep efficiency may, in some embodiments, be modeled as a constant, e.g., an average, value based on one or more sleep sessions and sleep session duration data for those respective one or more sleep sessions. For instance, a user may have a sleep efficiency of 0.94 which may be an average sleep efficiency over a specific period, such as the last 7 days, one month, or longer. If the user typically desires 8 hours of total sleep duration per sleep session, i.e., the user's selected sleep duration is 8 hours, then the sleep session duration that the user will likely need in order to attain 8 hours of total sleep may be estimated by dividing the selected sleep duration by the sleep efficiency, e.g., 8 hours divided by 0.94, which results in a target sleep session duration of approximately 8 hours and 30 minutes. This may also be thought of as multiplying the selected sleep duration by a factor that is based on the sleep efficiency, e.g., a factor such as 1/sleep efficiency. This target sleep session duration, in turn, may be subtracted from the scheduled waketime in order to determine a target bedtime, e.g., if the user's scheduled waketime is 7:00 a.m., then to reach 8 hours of total sleep duration in the designated sleep states, the target sleep duration of 8.5 hours may be subtracted from the scheduled waketime to yield a target bedtime of 10:30 PM the night before.

Sleep efficiency may be accounted for in determining a target bedtime in a variety of different ways. In some target bedtime determination techniques, sleep efficiency may be determined directly, as in the above example, and then applied to a selected sleep duration to arrive at a target sleep session duration which may then be subtracted from a scheduled waketime to determine the target bedtime. In other techniques, the sleep efficiency may be inherently accounted for in the target bedtime without ever directly calculating it—in either case, however, sleep efficiency is accounted for in the target bedtime. An example of such inherent accounting for of sleep efficiency is discussed below.

Figure 29:
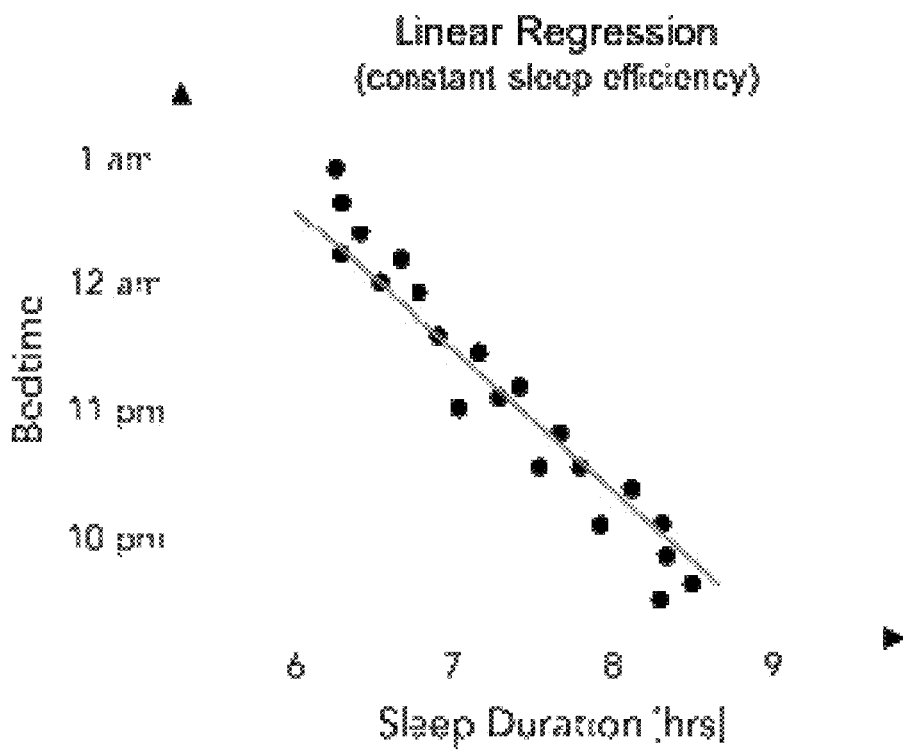
FIG. 29 is a plot of an example linear regression model fit to a plurality of sleep data points.

FIG. 29 depicts a graph of a linear relationship between sleep state duration data for one or more sleep sessions and sleep session bedtime data for those respective one or more sleep sessions. Such data for a plurality of sleep sessions with generally consistent waketimes (e.g., approximately 7:30 AM) are plotted in the graph with sleep state duration in hours on the x-axis and bedtime on the y-axis; the line through the data points represents a linear relationship, e.g., as determined by applying a linear regression model to the data, between these two data points that inherently accounts for sleep efficiency. Thus, for example, if the scheduled waketime is 7:30 AM, then the regression model that is applied to the data of FIG. 29 may be used to determine the target bedtime as a function of the selected sleep duration. In this example, if the selected sleep duration is 8 hours, then the target bedtime that may be calculated based on the regression model may be 10:22 PM, which represents a target sleep session duration of 9 hours and 8 minutes; the sleep efficiency for such a sleep session would be 8 hours divided by 9.14 hours, or 87.5%. Similarly, if the selected sleep duration is 7 hours, then the target bedtime that may be calculated based on the linear regression model in this example is 11:30 PM, which represents a target sleep session duration of 8 hours; the sleep efficiency for such a sleep session would also be 87.5% since the sleep efficiency that is inherently reflected by the linear regression model is a constant sleep efficiency. This constant sleep efficiency is similarly observable if one calculates a target bedtime using the linear regression model for a selected sleep duration of 6 hours—the target bedtime for such a sleep duration would be 12:39 AM and the sleep session duration would be 6 hours 51 minutes, which, again, reflects an 87.5% sleep efficiency. Since the sleep data store may include the start time (the bedtime) and the end time (the waketime) for each sleep session in a plurality of historical sleep sessions, applying a linear regression model (or other data-fitting model) to such data may allow for direct determination of a target bedtime that accounts for sleep efficiency without requiring the separate determination of the actual sleep efficiency.

Sleep efficiency may also be accounted for in more sophisticated ways to allow for more refined determinations of target bedtime that are even more customized or personalized to the sleep habits of the user. In the example above, the linear relationship between bedtime and sleep duration assumes that sleep efficiency is individually uncorrelated to bedtime, waketime, and/or sleep state duration, e.g., constant, and for many users this assumption may not hold true in practice. For example, a user that wakes up at the same time every day (e.g., 7:00 a.m.) and goes to bed at different times may consequently spend different amounts of time in non-awake sleep states for each sleep session, e.g., each night. For sleep sessions where the user goes to bed late, the user may be more tired than usual, may fall asleep faster than normal, and therefore may have more efficient sleep. Conversely, if the user goes to sleep earlier than normal, they may not be as tired and it may take them more time to fall asleep, thereby lowering their sleep efficiency. This may create a non-linearity in the relationship between sleep state duration data for one or more sleep sessions and sleep session duration data for the corresponding one or more sleep sessions because the user's sleep efficiency is correlated with bedtime such that, for instance, later bedtimes may result in increasingly efficient sleep and thus more sleep than a linear relationship may predict.

Therefore, as discussed herein below, in some embodiments the calculation of the target bedtime may account for a variable sleep efficiency that may be affected by one or more factors and thus be more accurate than a sleep efficiency that is assumed to be constant.

In regression model-based approaches to determining target bedtime, the regression model may be any type of regression model including, but not limited to, a linear regression model, a nonlinear regression model, a parametric regression model, a nonparametric regression model, a semiparametric regression model, and a multivariate linear regression model. For instance, a parametric model (e.g., a polynomial) may be fit to sleep data including sleep state duration data, waketimes, sleep session duration data, and/or bedtimes to account for non-linear relationships between the variables. For instance, the recommended bedtime may be provided using a function modeled on:

$$\text{target bedtime} = \sum_{n=0}^{N} \alpha_n (\text{sleep state duration data})^n$$

in which $\alpha_n$ are the weights for each polynomial term (up to order N) that could be determined via regression fitting. For example, in the context of a linear regression, an example of such a function may have only two terms, the coefficients of which ($\alpha_0$ and $\alpha_1$) are determined via linear regression analysis of sleep data for one or more users, e.g., of the user for which the target bedtime is being determined, and which may inherently account for the effects of sleep efficiency on the target bedtime for a given selected sleep duration since the linear regression model (or whatever regression model is used) will have been "trained" or calibrated using sleep data that is reflective of such sleep efficiency. In such an example, $\alpha_0$ may represent the individual's average waketime less the average amount of time spent in a non-efficient sleep state during an average sleep session, and $\alpha_1$ may be another coefficient that encodes sleep efficiency with respect to sleep duration—if sleep efficiency changes linearly with sleep state duration, then $\alpha_1$ would be above or below −1, but not exactly −1, such that:

$$\text{target bedtime} = \alpha_0 + \alpha_1 (\text{selected sleep duration}) =$$
$$\text{average waketime taking into account sleep efficiency} -$$
$$\text{selected sleep duration taking into account sleep efficiency}$$

Figure 30:
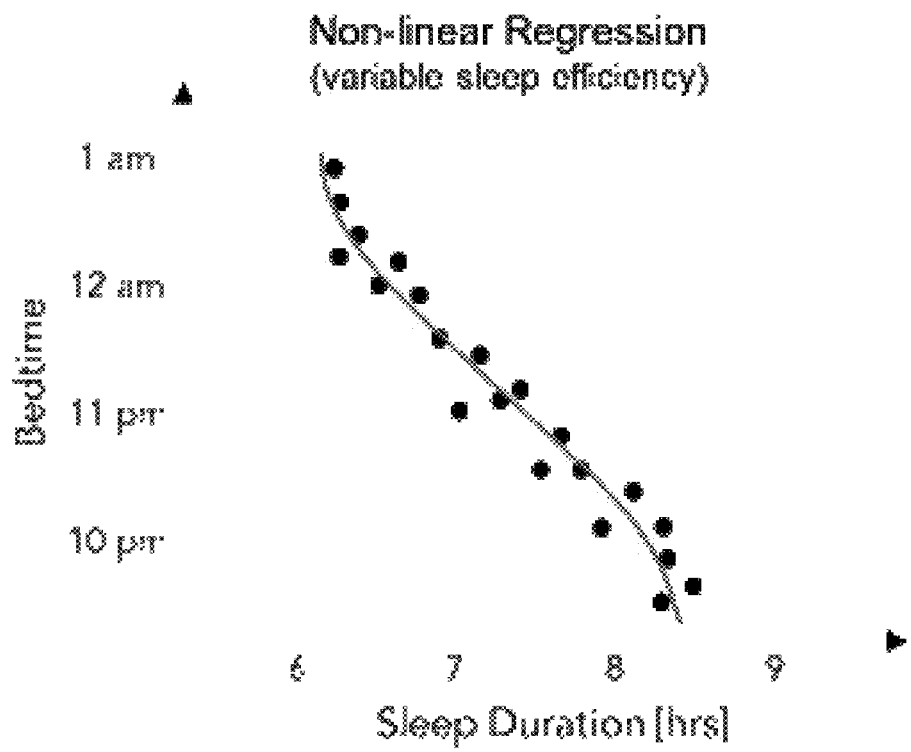
FIG. 30 is a plot of an example non-linear regression model fit to the plurality of sleep data points of FIG. 29.

The training of the regression model may be further enhanced, for example, by using a subset of training data (sleep data) that is within a certain threshold range of the scheduled waketime, if desired. FIG. 30 depicts a parametric regression model fit to the data of FIG. 29. As can be seen, the curve in FIG. 30 conforms more closely to the data than in FIG. 29, and may therefore more accurately account for sleep efficiency. It is to be understood that the above example is merely one example of how sleep data may be used to train a regression model. It will be appreciated that other variations may train a regression model using other combinations of sleep data, e.g., target bedtime may be determined according to a regression model that is a function of scheduled waketime rather than selected sleep duration (using a subset of sleep data that is inclusive of the selected sleep duration, for example), and that the coefficients used may represent a variety of different.

Other regression model techniques may include lasso, ridge, Bayesian, and maximum likelihood methods. In some such embodiments, the regression model may explicitly include waketimes and/or the measured sleep efficiency in the regression model. Collinearity in the curve fit may also be mitigated by any known technique including, for instance, Principal Components Analysis. Additionally, known uncertainties in the calculations and/or estimates of bedtime and/or sleep state duration may be included in the regression model, e.g., via maximum likelihood fitting. In some embodiments, outliers may be accounted for in the regression model to improve the fit by, for example, using Random Sample Consensus or other known iterative fitting methods.

In some implementations, the influence of various factors, such as those discussed herein, may be accounted for as co-variates that are used in the regression model. For example, if desired waketime is to be accounted for, then the above framework may be modified to:

$$\text{target bedtime} = \sum_{n=0}^{N} \alpha_n (\text{selected sleep duration})^n + $$
$$\beta(\text{scheduled waketime} - \text{average waketime})$$

in which β may be a factor determined using regression analysis and the covariate term β (scheduled waketime—average waketime) may shift the target bedtime by an amount dependent on the difference between the average waketime and the desired waketime. For example, if a linear regression model were to be applied, then the alpha and beta parameters or coefficients would be determined according using regression fitting.

Some example non-parametric methods for the regression model include, for instance, K Nearest Neighbors (KNN), Random Forest regression, and Gaussian process regression. For example, in the KNN case, a user with historical sleep data, a scheduled waketime, and/or a selected sleep duration, the sleep session duration data and corresponding sleep state duration data for the plurality of sleep sessions included in the regression model may be associated with, e.g., may be the nearest, K sleep sessions with similar waketimes, e.g., waketimes that are within a first threshold amount of the scheduled waketime. For example, the first threshold may be ±15 minutes of the scheduled waketime of 7:30 a.m. and the sleep sessions include in the regression model are those sleep sessions with waketimes ranging from 7:15 a.m. to 7:45 a.m.

Similarly, the sleep session duration data and corresponding sleep state duration data for the plurality of sleep sessions included in the regression model may be associated with, e.g., may be the nearest, K sleep sessions with similar sleep state duration data, e.g., with selected sleep duration data that is within a second threshold amount, e.g., within ±15 minutes, of the selected sleep duration.

In some implementations, the sleep session duration data and corresponding sleep state duration data for the plurality of sleep sessions included in the regression model may also be associated with, e.g., may be the nearest, K sleep sessions with waketimes that have occurred on the same day of the week as the day of the week on which the scheduled waketime occurs. For example, if the user has a scheduled waketime that occurs on a Monday, then the data included in the regression model may be associated with sleep sessions with waketimes that have also occurred on a Monday. The resulting bedtime recommendation may be the average bedtime from those K nights, or some pre-chosen quantile from the distribution of bedtimes. This may allow for variations in sleep efficiency that are day-dependent to be taken into account—for example, a person may generally be more tired on Sunday nights due to participating in soccer games on Sunday afternoons, and may therefore have a higher sleep efficiency during sleep sessions starting on Sunday evenings and ending on Monday mornings.

In some embodiments, the regression model may account for one or more of: one or more specific days of the week, a specific time of year, holidays, workdays of the user, non-workdays of the user, a seasonal time change, a geographic location, travel by the user between at least two time zones, exercise of the user, and a duration of daylight in a day. In some instances, a particular user's sleep data may not have data points that allow for such factors to be taken into account, in which case data from other users may be analyzed and used as a stand-in for data associated with that user.

For example, day of the week may be included in the regression model since many users have distinct bedtimes, waketimes, and sleep state durations on weekdays and weekends. For instance, some users tend to go to bed later, sleep longer, and/or sleep in later on weekends as compared to weekdays. The relationships between these variables can be distinct on weekdays and weekends. Therefore, for instance, the regression model may be fit to sleep data associated with sleep sessions that have waketimes on weekdays (when calculating target bedtimes that are for waketimes that are on weekdays), while in another instance, the regression model may be fit to sleep data associated with sleep sessions that have waketimes on weekends (when calculating target bedtimes that are for waketimes on weekends).

Similarly, time of year may be an included covariate to the regression model. Sleep behavior generally changes with season, and is typically correlated with the amount of sunlight per day (i.e., day length), which in turn generally has a strong effect on the circadian rhythm. For example, a user may sleep 15 minutes more on average during the winter than the summer. Specific nights of data, or sleep sessions that may start and/or end near a holiday (e.g., a user may start a sleep session past midnight of a holiday) may be excluded or de-weighted to improve the regression model. For example, sleep behavior on officially recognized holidays, even if on a weekday, may look more like a weekend (e.g., with later bedtimes, longer sleep state durations, and later waketimes). Time changes, such as seasonal and daylight savings, may also be accounted for by the regression model; such time changes generally effect sleep behavior due to the circadian rhythm not adjusting to time changes immediately. The regression model may exclude sleep data or de-weight sleep data around time change dates because that data may, in some instances, be less representative of the underlying relationship between bedtime, waketime, and sleep state duration for a user.

Activity level in the hours before bedtime may also be accounted for in the regression model. Such activity levels may be used to predict time to fall asleep; for example, if a user is highly active within a certain time period before the scheduled bedtime, the user may have more trouble falling asleep and may need to try to fall asleep sooner to achieve the sleep goal. Likewise, heart rate in the hours before bedtime may also be accounted for in the regression model and may be used to predict time to fall asleep. For example, if the user has elevated heart rate with a certain time period before the scheduled bedtime, the user may have more trouble falling asleep and may need to try to fall asleep sooner to achieve the sleep goal. The target bedtime may, in such cases, be determined based on bedtimes for sleep sessions in the sleep data store that are associated with similar elevated heart rates that occur within that time period prior to the sleep session bedtime. As noted above, the target bedtime may be based, at least in part, on the sleep efficiency of other users of other biometric monitoring devices or the sleep efficiency of the user of the biometric monitoring device. Accordingly, the target bedtime may be based, at least in part, on sleep data associated with the user of the biometric monitoring device and/or sleep data associated with other users of other biometric monitoring devices. As stated above, the sleep data associated with the other users may be stored as corresponding sleep logs in the sleep log data store; such sleep data may also be derived from sensor data generated by the other biometric monitoring devices of the other users.

Generally speaking, the target bedtime (as well as recommended sleep durations, as discussed earlier with respect to the various GUIs dealing with establishing a selected sleep duration) for a user may be determined from data that is associated with that user, as such data will best reflect that particular user's sleep behavior, efficiency, and sleep needs. However, in situations where there is insufficient data or no data associated with that user that may be used to determine a target bedtime (or, for example, a typical sleep duration), sleep data from other users may be used as a stand-in for data associated with that user.

For instance, the aforementioned regression models may be applied to sleep data associated with the user and/or sleep data associated with other users. In some such embodiments, there may not be sufficient to model the user's sleep data, but it may be beneficial to determine a target bedtime for the user even when little or no sleep data has been obtained from the user. For example, the target bedtime for the user may be determined based, at least in part, on the application of a regression model to sleep data from other users of similar demographics and/or living in the same geographic region.

In some implementations, the target bedtime may also be based, at least in part, on a proper subset of one or more of one or more specific days of the week, a specific time of year, holidays, workdays of the user and/or other users, non-workdays of the user and/or other users, a seasonal time change, a geographic location, travel by the user and/or other users between at least two time zones, exercise of the user, and a duration of daylight in a day. For example, if the user's scheduled waketime is on a weekday, then the target bedtime may be based, at least in part, on the user's historical sleep data associated with that same weekday. For another example, as mentioned above, if the user's scheduled waketime is on a weekday but that weekday is also a holiday, then the target bedtime may be based, at least in part, on the user's historical sleep data associated with that same holiday, a weekend day, a different holiday, and/or other users' sleep data associated with that same holiday. In such implementations, the target bedtime may account for a sleep efficiency that may vary based on such factors, e.g., the sleep efficiency may be based, at least in part, on one or more of historical sleep efficiency data associated with one or more of: a proper subset of one or more specific days of the week, a specific time of year, holidays, workdays of the user, non-workdays of the user, a seasonal time change, a geographic location, travel by the user between at least two time zones, exercise of the user, and a duration of daylight in a day. For example, if the user's scheduled waketime is on a weekday, then the sleep efficiency may be based, at least in part, on the user's historical sleep efficiency data associated with that same weekday.

The target bedtime discussed above may be considered an "optimal bedtime" and such optimal bedtime may be further calculated, analyzed, and/or modified before being presented as a recommended bedtime that is included in the GUI. In some embodiments, the recommended bedtime discussed above is the optimal bedtime that is included in the GUI. Even if the target bedtime is not used as the recommended bedtime, the recommended bedtime will still be based on the target bedtime in some fashion, as will be seen in the examples below.

In some embodiments, the recommended bedtime may be selected so as to be at some regular hourly division, e.g., the closest quarter hour on the hour to the target bedtime. Thus, for example, a target bedtime of 11:24 PM may cause a recommended bedtime of 11:30 PM to be selected, whereas a target bedtime of 11:21 PM may cause a recommended bedtime of 11:15 PM to be selected. This may make it easier for a user to remember the recommended bedtime.

In some other such embodiments, the recommended bedtime may be before or after the optimal bedtime by a particular time, such as between about 1 and 30 minutes. For example, 15 minutes may be subtracted from the optimal bedtime such that the recommended bedtime is 15 minutes earlier than the optimal bedtime, thereby causing the user to think about going to bed earlier. This may be useful, for example, in situations where the sleep data for the user indicates that the user is consistently late by 10 to 20 minutes in actually going to bed by their recommended bedtime.

In some embodiments, the recommended bedtime may be based, at least in part, on the user's optimal weekday or optimal weekend bedtime, or on days of the week specified by the user.

In some other embodiments, the recommended bedtime may be based, at least in part, on the differences between average sleep state duration data for weekdays and weekends. For example, if the user sleeps longer on weekends than weekdays, it may indicate that the user is accumulating sleep debt during the week that making up for it on the weekend. Averaging sleep state duration data for the entire 7-day week may provide a more accurate representation of the user's sleep need than for just the work week (e.g., Monday through Friday). If the user's selected sleep duration is lower than his inferred sleep need, the recommended bedtime may be adjusted, e.g., with time added or subtracted to the target bedtime, to reduce the accumulation of sleep debt.

In some embodiments, the recommended bedtime may be based, at least in part, on how inconsistent the user's bedtime is for a certain period of time. For example, a user with an inconsistent bedtime may be provided with a recommended bedtime that is later than the optimal bedtime in order to achieve the user's selected sleep duration because such recommended bedtime may be a more achievable bedtime for the user.

In some embodiments, the recommended bedtime may be based, at least in part, on a forecast of the user's future bedtime which may be more appropriate for near-future behavior. For example, for a user with a long baseline of data (e.g., numerous months or years), the user's own sleep data may be modeled for the forecast while for users with insufficient data, sleep data of other similar users (e.g., similar demographics, activity level, and/or geographic location) may be used for the forecast. In some such embodiments, both the data of the user and other users may be used for the forecast. For instance, as noted above, the user's optimal bedtime may be based, at least in part, on the season or time-of-year. Because sleep behavior may have a seasonal component that is tied to the amount of daylight, sleep state duration may be lower in the summer compared to the winter on average, bedtimes may be later, and the accumulation of weekday sleep debt may be different. Such trends may be incorporated into the recommended bedtime by forecasting how the user's behavior may change in the near or long future. For example, when calculating a recommended bedtime for a user in North America in April, the average bedtime will trend later as the summer solstice approaches and the amount of daily sunlight increases.

Therefore, the recommended bedtime may be adjusted earlier in anticipation of this trend so that the user is more likely to achieve their selected sleep duration in the coming months as their bedtime naturally trends a bit later, thereby making it easier for the user to achieve the recommended bedtime and increasing user satisfaction (this may result in a shorter sleep duration than the selected sleep duration, however—this may nonetheless be desirable if it positively reinforces the user experience with the sleep tracking and scheduling functionality discusses herein). Alternatively, the recommended bedtime may be adjusted to be earlier than it otherwise would in anticipation of the user wanting to stay up later due to the longer days. The user may decide to stay up an extra hour past the recommended bedtime, but if the recommended bedtime has been shifted earlier by half an hour, then the user may only be going to bed by half an hour later with respect to the target bedtime than they otherwise would. Similarly, the recommended bedtime may be shifted in the opposite directions in preparation for winter months, e.g., a later bedtime may be provided that is more in-line with what the user is likely to do in the coming months. Recommending a bedtime that is responsive to the user's natural behavior is more likely to keep the user engaged with healthy sleep behavior rather than suggesting a bedtime that will be difficult to achieve.

As mentioned above, season may be a factor included in modeling sleep behavior and making bedtime recommendations. The seasonal changes are location dependent, largely on latitude, but may also depend on local climatic patterns, time zones, and/or cultural customs. When retrieving sleep data of other similar users for modeling and/or forecasting, location may be used as part of the similarity measure to account for these dependencies.

In some embodiments, long term behavior, rather than short term behavior, may be forecast and the recommended bedtime may therefore average out seasonal modulations. In some other embodiments, the recommended bedtime may be based, at least in part, on whether a time change (e.g., daylight savings time) has recently changed or is just about to. As mentioned above, time changes (e.g., daylight savings time) can disrupt a user's sleep behavior and bedtime. The recommended bedtime may be shifted earlier or later to help mitigate the effects of these changes. In some embodiments, the recommended bedtime may be based, at least in part, on age and/or knowledge of whether the user is working or retired. Sleep duration, sleep efficiency, bedtime, and/or amount of deep sleep may change with age. For example, weekday sleep duration decreases on average with age, except after retirement age where sleep duration starts to starts to increase again. Such trends may also be accounted for in the recommended bedtime.

In some embodiments, the optimal bedtime recommendation may be shifted from the target bedtime based, at least in part, on a value that is calculated experimentally (e.g., via A/B testing, multi-armed bandit testing, or parameter optimization experiments). For example, a cohort of users may be defined, (e.g., male runners in New York City, between 20 and 25 years of age, etc.), and some of these users may be separated into a control group while the remaining users may be placed into a testing group. Example tests may include determining if recommending a particular bedtime leads to more or less adoption from users in the control group as compared to a variant (e.g., that bedtime minus 10 minutes) that is recommended to the testing group. Accordingly, the recommended bedtime may be adjusted because a user is in a particular test or control group. Additionally, if such experiments indicate that a particular bedtime recommendation methodology is more likely to lead to a desired outcome (e.g., a more consistent bedtime), then the recommended bedtime for all users that are demographically similar to the cohort users may be adjusted accordingly.

Figure 31:
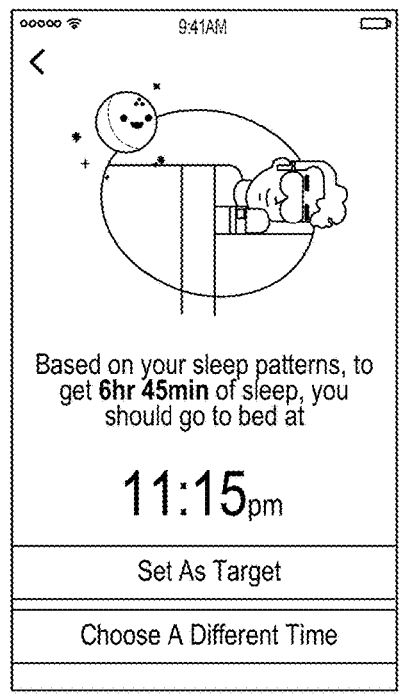
FIG. 31 is an example of a graphical user interface that may be used to recommend a personalized recommended bedtime to a user and to allow the user to confirm or reject the recommended bedtime for use as a selected bedtime.
Figure 32:
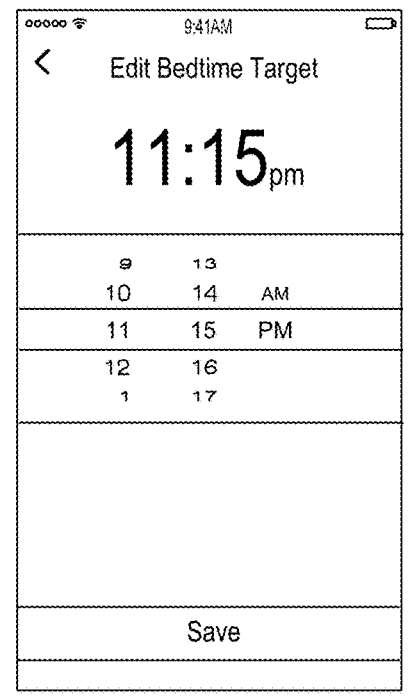
FIG. 32 is an example of a graphical user interface that may be used to allow the user to adjust the selected bedtime.

As stated above, generating the one or more personalized GUIs may include generating a GUI that includes the recommended bedtime (or the target bedtime, if the target bedtime is used as the recommended bedtime). As noted and described at length above, the recommended bedtime may be based, at least in part, on the sleep data for one or more users stored in the sleep log data store. FIG. 31 depicts a graphical user interface that includes a recommended bedtime 3102. As can be seen, the recommended bedtime of "11:45 pm" is included in the GUI, along with the selected sleep duration 3101 ("6 hr 45 min"). Two prompts 3103 may also be included in the GUI of FIG. 31 which may allow the user to confirm and store the recommended bedtime as the user's selected bedtime or to input a different time for the selected bedtime of the user. FIG. 32 depicts a graphical user interface to obtain a different recommended bedtime 3201 using prompt 3202. Similar to other GUIs described above, the user may input a bedtime which may be received and stored as the selected bedtime.

Establishing a Sleep Schedule—Setting Bedtime Reminders

In some embodiments, a bedtime reminder may also be displayed and/or presented to the user in advance of the selected bedtime order to remind the user to go to bed. In some embodiments, the memory may store instructions for further controlling the one or more processors to present to the user, via a notification mechanism, the bedtime reminder.

The bedtime reminder may be provided, at least in part, as a "notification" which may be one or more of a message, an auditory output, an electronic communication, an electromagnetic communication, a visual output, and a tactile output. For instance, the mechanism through which the notification may be conveyed may, generally speaking, be referred to as a notification mechanism. Notifications may be provided through a variety of media, and may, in some cases, require further action by an intermediate device before being perceptible by the person. For example, a biometric monitoring device may have a notification mechanism that includes a display or lights that are configured to display graphics or light up in order to catch the attention of a person (the notification, in this case, may refer to a signal that is sent to the lights or display that cause these components to light up or display graphics to a person; it may also refer to the light or graphics that is emitted or displayed by components receiving the signal in response to the signal). In some examples, the biometric monitoring device may have a notification mechanism that includes a speaker or other device capable of generating auditory output that may be used to provide the notification (the notification in this case may be a signal that is sent to a speaker or other audio device; it may also refer to the actual audio output that is generated by the audio device in response to the signal). In some other or additional examples, the notification mechanism may include a wireless interface and the notification may take the form of an electronic or electromagnetic communication, e.g., a wireless signal, that is sent to another device, e.g., a wearable fitness monitoring device such as a Fitbit activity tracker or a smartphone, associated with the person (the notification in this case may be an electromagnetic signal; it may also refer to any audio, visual, tactile, or other output generated by the receiving device in response to receipt of the signal). In such scenarios, the notification may still be generated or initiated by the notification mechanism even if the intended recipient device of the communication fails to be activated or otherwise fails to convey the notification to the person. The notification mechanism may be configured to generate and/or provide one or more notifications to the user, and may include one or more components that may be used to generate audio, visual, tactile, electromagnetic, or other types of notifications.

In various implementations, the notification may ultimately be provided using any of a variety of output mechanisms, i.e. notification mechanisms. In some implementations, the notification may include nothing more than a light on the fitness monitoring device that blinks intermittently when the user is to be reminded to go to bed. In other additional or alternative implementations, the notification may include other visual feedback, e.g., graphics, text on a display, etc.; audio feedback, e.g., melodies, speech, sound effects, etc.; tactile feedback, e.g., vibration, mild electric shock, etc.; electromagnetic signals to other devices to cause those other devices to provide feedback perceptible to the person, e.g., signals sent to smartphones, laptops, desktops, tablets, other fitness monitoring devices, etc.; and other forms of communicating with the person.

Figure 33:
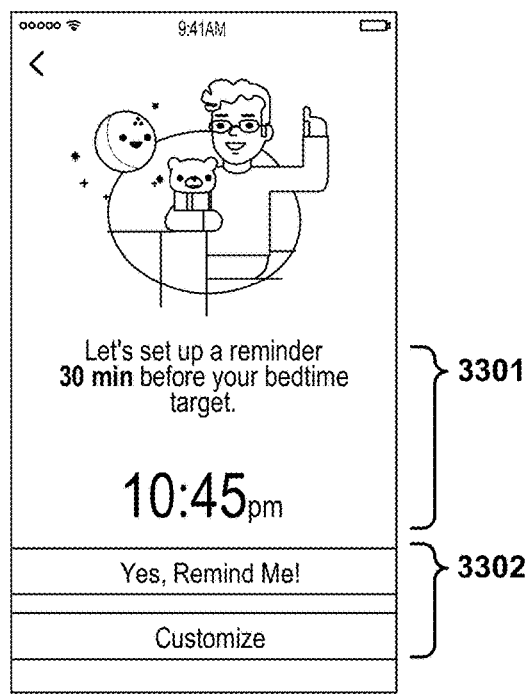
FIG. 33 is an example of a graphical user interface that may be used to establish a reminder in advance of a selected bedtime.

In some embodiments, generating the one or more personalized GUIs may further include generating a GUI to obtain timing information indicating one or more selected reminder times for a bedtime reminder and generating, for instance via the notification mechanism, the bedtime reminder based, at least in part, on the timing information. The reminder time may be the time at which the bedtime reminder is presented to the user; the timing information may be information that defines when the bedtime reminder is to be provided relative to the selected bedtime. FIG. 33 depicts a graphical user interface that may be used, at least in part, to obtain timing information 3301 related to a bedtime reminder. As can be seen, the GUI of FIG. 33 includes timing information 3301 that defines or establishes a selected reminder time for the bedtime reminder to be presented to the user, which here is 30 minutes before the selected bedtime, i.e., the recommended bedtime.

The time included in the GUI of FIG. 33 (e.g., "10:45 p.m.") may also be considered a recommended reminder time for the bedtime reminder. In some such embodiments, generating the one or more personalized GUIs may further include calculating the recommended reminder time for the bedtime reminder based, at least in part, on the recommended bedtime, and displaying the recommended reminder time as part of the GUI, like in FIG. 33. Here, the recommended reminder time is 10:45 p.m. which was calculated by subtracting 30 minutes from the selected bedtime. In other implementations, the user may simply define an offset time, e.g., 30 minutes before the selected bedtime.

Figure 34:
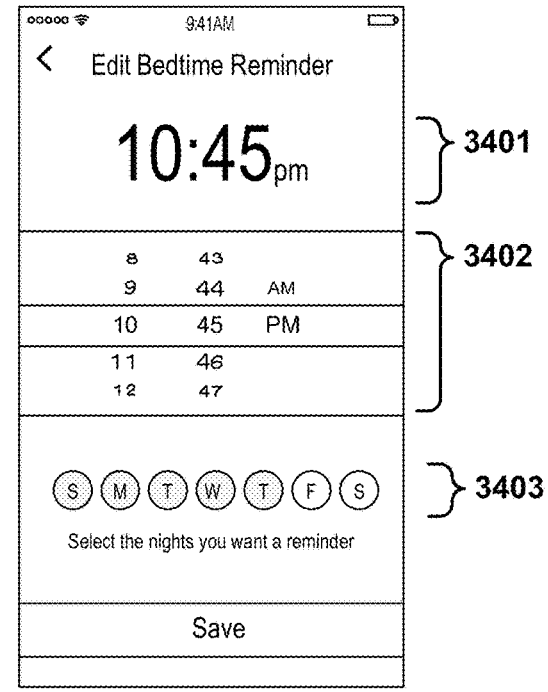
FIG. 34 is an example of a graphical user interface that may be used to allow the user to change timing information for a bedtime reminder.

There are also two prompts 3302 in FIG. 33 which allow the user to select the displayed selected reminder time as the selected reminder time such that it may be obtained and stored by the GUI, or to change the selected reminder time. FIG. 34 depicts a graphical user interface that may be used, at least in part, to obtain timing information related to a bedtime reminder. As can be seen, the user may, via prompts 3402 and 3403, input timing information 3401, such as a specific time as well as day, for the bedtime reminder to be generated, e.g., presented via the notification mechanism, to the user. Therefore, the GUI that is generated may obtain both timing information indicating one or more selected reminder times for a bedtime reminder as well as day information indicating one or more selected reminder days for the bedtime reminder. In such embodiments, generating the bedtime reminder, e.g., via the notification mechanism, may be based, at least in part, on the timing information and/or the day information.

Figure 35:
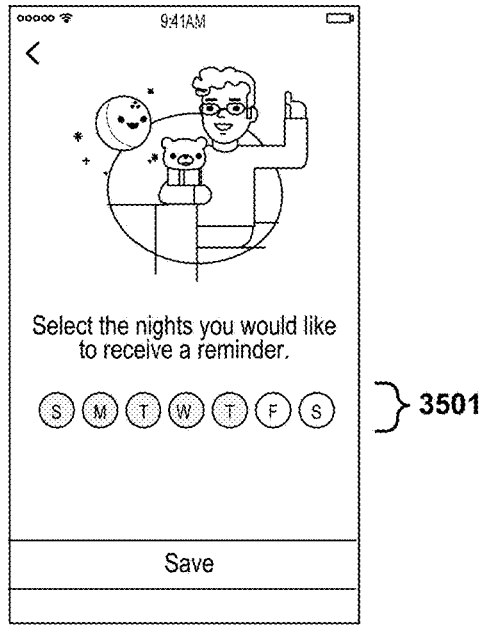
FIG. 35 is an example of a graphical user interface that may be used to allow a user to specify on which days to provide a bedtime reminder.

Similarly, in some embodiments, a different GUI may be generated to obtain day information indicating one or more selected reminder days for the bedtime reminder, and the generating of the bedtime reminder may be further based, at least in part, on the day information. For example, FIG. 35 depicts a graphical user interface that may be used, at least in part, to obtain day information related to a bedtime reminder. Like in FIG. 33, the GUI of FIG. 35 may obtain information 3501 relating to a reminder day or reminder days on which the bedtime reminder will be displayed. Such information may be a specific day and/or a grouping of days, such as weekdays or weekends.

As noted above, the bedtime reminder may be generated, such as by the notification mechanism, based, at least in part, on the day information and/or the timing information. In some embodiments, the bedtime reminder may include the recommended bedtime.

It should be noted that in many embodiments, the bedtime reminder may be sent before the user's recommended bedtime so that the user has adequate time to prepare for bed. This notification, e.g., warning window, may be set in several ways. For example, the user may set how many minutes before the recommended bedtime, e.g., the scheduled bedtime, the user would like to receive the bedtime reminder. The notification may also be personalized for each user based on how many minutes of low activity the user typically logs before the user falls asleep. Users who tend to wind down quickly before sleep time would need a shorter window to prepare for bed compared with users who typically have long periods of low activity before bed. The warning window may be adjusted based on whether or not the user has a history of reducing his activity level after receiving the reminder. If the user is detected to be more active than usual (e.g., by steps, metabolic equivalent units, workouts, elevated heart rate) in the hours before bed, the user's bedtime reminder may be adjusted earlier to recommend a longer winding down period so that the user is able to fall asleep in time to meet his selected sleep duration and scheduled waketime, e.g., a sleep goal and a wake goal.

The bedtime reminder may also have a snooze option. If the user does begin to lower their activity level, the alarm will go off again. The bedtime reminder may also use location as an input for determining whether or not the user is able to react to the alarm. For example, if the user is not at home, the alarm may be disabled to avoid discouraging the user who is in a situation out of their control (e.g., still at work, or at a bar).

The bedtime reminder may also function as a feedback loop or as an online learning model and learn over time when to remind a user at a time that is most likely to get the user to go to bed on time. For example, the bedtime reminder may be a system that may remind the user to go to bed 15 minutes before her recommended bedtime on one or more days. Then the bedtime reminder system may switch behavior and remind the user 20 minutes before her recommended bedtime for one or more days. It may similarly try different variants, and if one of those variants was more successful in getting the user to go to bed at the selected bedtime, then that variant may be adopted. Similarly, learnings about the most successful bedtime reminder variants from other users may be used to set bedtime reminders for users new to the feature. In the more general case, the bedtime reminder model may optimize for some other behavior of interest besides just maximizing the probability that the user will go to bed on time. For example, the system may try to optimize a more general cost function that maximizes engagement, and/or minimizes sleep debt accumulation, etc.

Scheduling the bedtime reminder may also be recommended in the morning, based on the sleep state duration data of the user for the previous sleep session. The schedule of the bedtime reminder may be adjusted to address accumulating sleep debt. The user may also be congratulated after a sleep session in the morning if the user achieved his or her bedtime target. Success may be defined as the user is asleep by her bedtime, and/or defined as the user is relaxed and lying down by her bedtime, attempting to meet the goal even if the user is unable to fall asleep. The bedtime may also be scheduled or recommended by a friend in a challenge form. Consistent bedtimes may also be a household, team, or group challenge where all members of the household need to achieve the bedtime in order to succeed.

Providing Feedback Regarding Individual's Sleep Behavior

As part of the present disclosure, determinations may be made from the sleep data as to how the user is performing with respect to the user's selected bedtime, scheduled waketime, and/or selected sleep duration, and additional GUIs may be generated that include such determinations and/or include new recommendations for a bedtime, waketime, and/or sleep duration based, at least in part, on such determinations.

Figure 37:
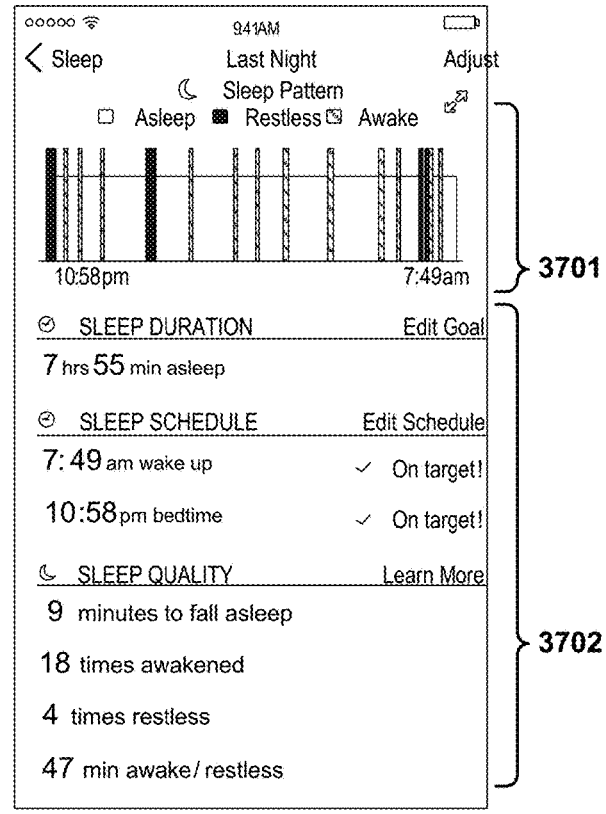
FIG. 37 is another example of a graphical user interface that may be used to provide summary information regarding sleep data and to compare sleep data against desired sleep goals.
Figure 36:
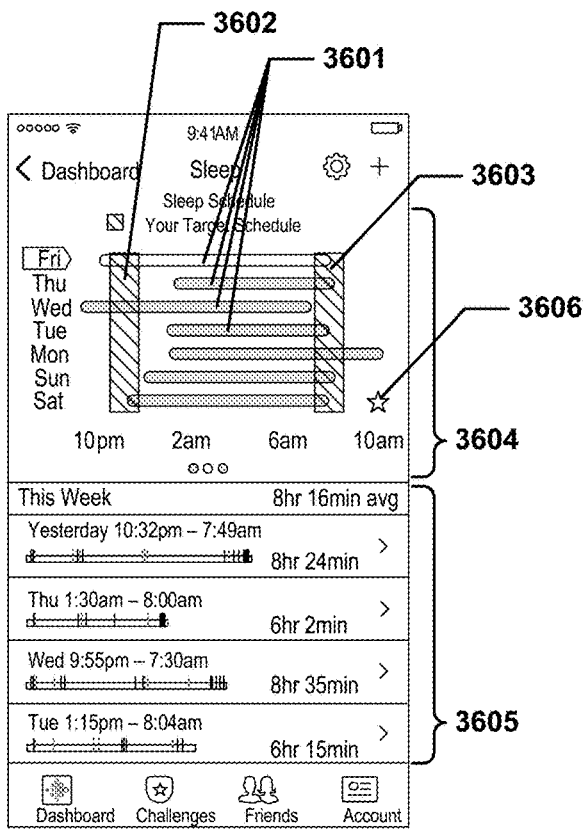
FIG. 36 is an example of a graphical user interface that may be used to provide summary information regarding sleep data and to compare sleep data against desired sleep goals.

In some embodiments, generating the one or more personalized GUIs may include determining, based on the sleep data of the user, how the user's sleep performance compares with the user's selected or desired sleep performance. For example, a determination may be made, for each of a plurality of sleep sessions, as to whether or not the user's actual bedtime, actual waketime, sleep state duration, and/or sleep session duration were within some acceptable range or threshold of the selected bedtime, the scheduled waketime, selected sleep duration, and/or the predicted sleep session duration (which may be based on the target sleep session duration and which, generally speaking, is equivalent to the time span bracketed between the selected bedtime and the scheduled waketime). The user's performance for such sleep sessions, as compared against the selected values, may be displayed on a GUI such as that shown in FIG. 36, which shows various sleep data points 3601 on timelines 3604 for the most recent seven days of sleep logs. As can be seen in FIG. 36, the selected bedtimes and the scheduled waketimes may be indicated with cross-hatched areas 3602 and 3603 that represent tolerance bands or thresholds, e.g., ±15 minutes, from the selected bedtimes and the scheduled waketimes (which would be located, for example, in the middle of such tolerance bands). The user's sleep data may be considered to be "on target" when the actual bedtimes and the actual waketimes that the user experiences are within the tolerance bands or thresholds, and such on-target behavior may be indicated using a graphical indicator, such as goal achievement indicator 3606. More informative timelines 3605 may also be included to show periods of restlessness or wakefulness during a sleep session for such days. FIG. 37 depicts a different graphical user interface that includes summary information 3702 regarding a single sleep session, including total sleep duration, the actual bedtime, the actual sleep time, how long it took the user to fall asleep (based on biometric monitoring device data), and total amount of time awake and/or restless during the sleep session. Also displayed is a timeline 3701 indicating which sleep states the person was in at any given point in the sleep session. In the case where a user is on-target for one or more of these parameters for a given sleep session, the GUI may be configured to display a congratulatory message, e.g., "On target!," regarding the user's achievement with respect to that parameter.

If the user is not on-target with respect to one or more of the selected bedtime, the scheduled waketime, selected sleep duration, and/or the predicted sleep session duration, then a personalized GUI may be generated that suggests one or more alternate settings for the selected bedtime, the scheduled waketime, the selected sleep duration, and/or the predicted sleep session duration. For example, if the user consistently misses attaining the selected sleep duration by 20 minutes, then the user may be presented with a personalized GUI that suggests that the user should consider a selected bedtime that is 30 minutes earlier than the current setting. In other implementations, the sleep data from other users that exhibited a similar inability to meet a similar target sleep metric but who then adjusted their sleep patterns to meet that metric may be analyzed to determine which of these parameters typically resulted in successful behavior modification of the users when adjusted. For example, in the example above, the sleep logs in the sleep log data store may be analyzed to locate other users that had similar (within ±15 minutes, for example) selected bedtimes, scheduled waketimes, and selected sleep durations and that also consistently missed their selected sleep durations by approximately 20 minutes (e.g., 20 minutes ±10 minutes); the sleep data from these identified users may be further analyzed to determine if they made any adjustments to their selected bedtime and whether they attained their selected sleep duration subsequent to such an adjustment. If so, then that adjustment (or a representation thereof, e.g., an average of the adjustment) may be used as the basis for recommending a similar adjustment to the user. For example, if such users are identified and analysis indicates that 70% of those users re-scheduled their selected bedtime for 30 minutes earlier, on average, than their previous settings, then the user may be provided with a revised recommended bedtime that is 30 minutes earlier than their current bedtime.

Once a user has been guided through setting a selected sleep duration and a selected bedtime, one or more additional GUIs may be generated to allow the user to easily edit and revise these settings without repeating the more involved guided/coached set up discussed above. For example, FIG. 38 depicts a GUI that may be generated to allow a user to easily change their scheduled waketime 3803, selected bedtime 3802, and/or selected sleep duration 3801, as well as a prompt 3804 to turn on or off a bedtime reminder and another prompt 3805 to allow the user to change the bedtime reminder timing information. By tapping on any of the indicated settings, the user may be taken to a new GUI (not shown) that allows for modification of such parameters by the user.

It is to be understood that the GUIs discussed above are merely one example of how sleep tracking functionality may be implemented for a user of a biometric monitoring device, and that there may be other techniques and GUIs that may be used instead that are nonetheless within the scope of this disclosure. The GUIs discussed above may also be implemented in a partial manner, e.g., the GUIs may not include GUIs geared towards introducing sleep tracking to a new user, but may instead proceed directly to the setting of a selected bedtime based on a user's accumulated sleep data (or on other users' sleep data, e.g., if the user has not accumulated sufficient sleep data of their own yet).

Some aspects of the present disclosure may occur in particular sequences or orders. For a first example, a determination may be made as to whether a user has a particular number of sleep logs stored in the sleep log data store (e.g., more than 5 sleep logs). If the user does not have the particular number of sleep logs, then GUIs associated with a new user may be generated, such as FIGS. 7 through 17. Once the GUIs associated with the new user have been generated, the sleep data (as described above) may be obtained and stored in the sleep log data store (as also described above); another determination may also be made as to whether a given number of sleep logs have been stored within a period of time (e.g., whether more than 5 sleep logs have been stored within 14 days).

If the determination is that the requisite number of sleep logs have been gathered, then additional determinations may be made as to whether the user has edited a selected sleep duration (i.e., sleep goal), whether the user has more a specific number of sleep logs within a period of time (e.g., more than 5 sleep logs within 14 days), and/or whether the user's sleep state duration data indicates that the user is within a specific threshold of the selected sleep duration. If the user has not edited this sleep goal, does not have more than the requisite number of sleep logs within the period of time, and/or the user's sleep state duration data does not indicate that the user is within the specific threshold, then GUIs associated with selecting a selected sleep duration, waketime, waketime alarm, recommended bedtime, and/or bedtime reminder may be generated. For instance, this may include FIGS. 18-28 and 31-34. However, if one or more of the determinations are opposite, then different GUIs may be generated, such as GUIs associated with selecting a waketime, waketime alarm, recommended bedtime, and/or bedtime reminder.

It should be noted that each of the GUIs described herein and shown is not an exhaustive list of the GUIs that may be generated as part of this disclosure. Furthermore, each and every feature described and shown may be included in one or more of the other GUIs; such features and information in the GUIs are not mutually exclusive of each and every other feature and information.

It is also to be understood that the techniques discussed above may be implemented as methods, as well as systems or devices configured, using computer-executable instructions stored in memory, so as to cause one or more processors to perform such methods. It is to be further understood that such computer-executable instructions may also be implemented in non-transitory form as computer-executable instructions that are stored on a storage device, e.g., in a computer-readable memory.

Importantly, the present invention is neither limited to any single aspect nor implementation, nor to any combinations and/or permutations of such aspects and/or implementations. Moreover, each of the aspects of the present invention, and/or implementations thereof, may be employed alone or in combination with one or more of the other aspects and/or implementations thereof. For the sake of brevity, many of those permutations and combinations will not be discussed and/or illustrated separately herein.

Embodiments discussed herein may provide solutions to a number of technical problems. For example, embodiments that generate suggested sleep-tracking parameters solve the technical problem of providing a meaningful user interface to a user. Such may be the case because those embodiments may generate a user interface with information that is relevant to the user, rather than provide default values that characterize, say, a general population. As described above, these parameters may include suggested waketime, sleep duration, bedtime, and the like. Thus, such embodiments may provide comparatively accurate information and suggestions to a user base that includes users with a wide variety of different sleep habits and needs.

Embodiments discussed herein may also provide solutions for increasing a user's engagement with a fitness monitor that tracks sleep. For example, embodiments may determine when to trigger the presentation or introduction of a sleep-related tracking feature. Such may be the case when embodiments selectively determine when to introduce a sleep consistency goal. In some cases, an embodiment may first introduce a sleep duration goal and then, after a determinable period (as may be determined based on historical sleep logs, for example), introduce a sleep consistency goal, e.g., to promote or encourage consistent bedtimes and waketimes, on-top of the sleep duration goal. Thus, such embodiments may provide comparative improvements for systems to retain and engage a user base compared, for example, with systems that do not provide such a staged or gradual introduction to sleep consistency tracking.

What is claimed is:

1. A method of generating one or more graphical user interfaces for setting a sleep schedule of a user of a biometric monitoring device, the method comprising:
   determining that an account assigned to the user is associated with less than a first number of sleep logs in a sleep log data store, wherein each sleep log includes sleep data derived from sensor data generated by the biometric monitoring device for a sleep session, the sleep data for each sleep log specifying various sleep states of the user for that respective sleep session;
   causing, responsive, at least in part, to the determination that the account assigned to the user is associated with less than the first number of sleep logs in the sleep log data store, a first set of one or more graphical user interfaces to be displayed to the user, wherein at least one graphical user interface of the first set of one or more graphical user interfaces to be displayed to the user includes a sleep duration user interface element configured to allow the user to specify a selected sleep duration of the user for one or more first future sleep sessions of the user, and the first set of one or more graphical user interfaces lack a scheduled waketime user interface element configured to allow the user to specify a scheduled waketime in association with the selected sleep duration of the user;
   obtaining the selected sleep duration specified by the user;
   responsive to obtaining the selected sleep duration, determining a configuration for the biometric monitoring device, the configuration for the biometric monitoring device being determined by:
      determining a model of the biometric monitoring device;
      comparing the model to a list of biometric monitoring devices; and
      retrieving the configuration of the biometric monitoring device from the list of biometric monitoring devices, the configuration indicating that the biometric monitoring device has one of automatic sleep tracking functionality and manual sleep tracking functionality;
   responsive to determining the biometric monitoring device is configured for automatic sleep tracking, causing a first graphical interface to be displayed the user, the first graphical user interface including one or more instructions specific to using the biometric monitoring device for the automatic sleep tracking;
   responsive to determining the biometric monitoring device is configured for manual sleep tracking, causing a second graphical interface to be displayed to the user, the second graphical user interface including one or more instructions specific to using the biometric monitoring device for the manual sleep tracking;
   obtaining sleep data for one or more sleep sessions of the user, wherein the sleep data for each sleep session includes sleep state duration data representative of the total amount of time the user spent in a subset of non-awake sleep states during that sleep session;
   storing the sleep data in the sleep log data store as one or more sleep logs associated with the account assigned to the user; and
   comparing the sleep state duration data for one or more of the sleep logs stored in the sleep log data store with the selected sleep duration.

2. The method of claim 1, wherein causing the first set of one or more graphical user interfaces to be displayed further includes:
   causing a suggested sleep duration to be displayed in a graphical user interface element of at least one graphical user interface of the first set of one or more graphical user interfaces, wherein the suggested sleep duration is based on one or more of: a default value and a target sleep duration determined based on one or more of sleep logs stored in the sleep log data store and including sleep data derived from sensor data generated by other biometric monitoring devices of other users.

3. The method of claim 2, further comprising:
   obtaining, after the display of the suggested sleep duration, a second selected sleep duration specified by the user.

4. The method of claim 3, further comprising:
   obtaining a second selected sleep duration after the display of the suggested sleep duration.

5. The method of claim 1, further comprising:
   determining that the selected sleep duration is not within a threshold amount of a default sleep duration value; and
   causing, based on the determination that the selected sleep duration is not within the threshold amount of the default sleep duration value, a suggested sleep duration to be displayed in a graphical user interface element of at least one graphical user interface of a second set of the one or more graphical user interfaces, wherein the suggested sleep duration is based on one or more of: a default value and a target sleep duration determined based on one or more sleep logs stored in the sleep log data store and including sleep data derived from sensor data generated by other biometric monitoring devices of other users.

6. The method of claim 1, wherein the determining that the account assigned to the user is associated with less than the first number of sleep logs in the sleep log data store is evaluated based on sleep logs associated with the account assigned to the user and associated with sleep sessions that occurred within a first period of time.

7. The method of claim 1, wherein causing the first set of one or more graphical user interfaces to be displayed further includes:
   causing information associated with average recommended sleep durations of a group of people to be displayed in a graphical user interface element of at least one graphical user interface of the first set of one or more graphical user interfaces.

8. The method of claim 1, wherein causing the first set of one or more graphical user interfaces to be displayed further includes causing information associated with the selected sleep duration, other than the selected sleep duration, to be displayed in a graphical user interface element of at least one graphical user interface of the first set of one or more graphical user interfaces.

9. The method of claim 1, wherein causing the first set of one or more graphical user interfaces to be displayed further includes:
causing the display of sleep state duration data of the user for at least one of the one or more sleep sessions.

10. The method of claim 9, wherein causing the second set of one or more graphical user interfaces to be displayed further includes:
calculating, in response to a determination that the sleep state duration data of the user for one or more of the one or more sleep sessions is outside a threshold amount from the selected sleep duration, a recommended sleep duration, wherein the recommended sleep duration is based on sleep data in sleep logs for one or more users that are stored in the sleep log data store, and
causing the recommended sleep duration to be displayed in a graphical user interface element of at least one graphical user interface of the second set of one or more graphical user interfaces.

11. The method of claim 9, further comprising:
obtaining a scheduled waketime of the user for one or more second future sleep sessions of the user after determining that the account assigned to the user is associated with at least the second number of sleep logs in the sleep log data store.

12. The method of claim 1, further comprising:
determining, after the obtaining sleep data for one or more sleep sessions of the user and the storing the sleep data in the sleep log data store, that the account assigned to the user is associated with at least one or more of: a second number of sleep logs in the sleep log data store and a second time period elapsed since the selected sleep duration was obtained; and
causing, in response to the determination that the account assigned to the user is associated with at least one or more of: the second number of sleep logs in the sleep log data store and the second time period elapsed since the selected sleep duration was obtained, a second set of one or more graphical user interfaces to be displayed to the user.

13. The method of claim 12, wherein the causing the recommended sleep duration to be displayed in a graphical user interface element of at least one graphical user interface of the second set of one or more graphical user interfaces includes:
causing an incremented recommended sleep duration to be displayed in a graphical user interface element in each of a series graphical user interfaces of the second set of one or more graphical user interfaces, wherein each incremented recommended sleep duration is greater than the previously displayed incremented recommended sleep duration, and wherein each incremented recommended sleep duration is associated with a different future sleep session.

14. The method of claim 12, further comprising:
obtaining a second selected sleep duration after causing the recommended sleep duration to be displayed.

15. The method of claim 12, wherein the recommended sleep duration is further based on one or more of: a look-up table, demographics of the user, one or more specific days of the week, a specific time of year, holidays, workdays of the user, non-workdays of the user, a seasonal time change, a geographic location, travel by the user between at least two time zones, exercise of the user, and a duration of daylight in a day.

16. The method of claim 15, wherein causing the second set of one or more graphical user interfaces to be displayed further includes:
calculating, after determining that the account assigned to the user is associated with at least a third number of sleep logs in the sleep log data store, a recommended waketime based on waketimes derived from the sleep data associated with the user stored in the sleep log data store, and
causing the recommended waketime to be displayed in a graphical user interface element of at least one graphical user interface of the second set of one or more graphical user interfaces.

17. The method of claim 16, wherein:
the calculation on which the recommended bedtime is based further accounts for, at least in part, the selected sleep duration of the user.

18. The method of claim 16, wherein:
obtaining the recommended bedtime is further based on a recommended waketime that is used as the scheduled waketime.

19. The method of claim 16, wherein:
the sleep efficiency is representative, at least in part, of a correlation between sleep state duration data for one or more sleep sessions associated with one or more sleep logs stored in the sleep log data store and sleep session duration data for the corresponding plurality of sleep sessions,
the sleep state duration data for each sleep session is representative of the total amount of time the user that is associated with the sleep session spent in a subset of non-awake sleep states during that sleep session, and
the sleep session duration data for each sleep session is representative of the total duration of that sleep session.

20. The method of claim 19, wherein the bedtime reminder includes information regarding the recommended bedtime.

21. The method of claim 19, wherein causing the second set of one or more graphical user interfaces to be displayed further includes:
calculating a recommended reminder time for the bedtime reminder based on the recommended bedtime, and
causing the recommended reminder time to be displayed in a graphical user interface element of at least one graphical user interface of the second set of one or more graphical user interfaces.

22. The method of claim 19, further comprising:
obtaining day information indicating one or more selected reminder days for the bedtime reminder, wherein the generating of the bedtime reminder is further based on the day information.

23. The method of claim 19, wherein:
the generating the bedtime reminder includes providing a notification, and
the notification is one or more of: a message, an auditory output, an electronic communication, an electromagnetic communication, a visual output, and a tactile output.

24. The method of claim 16, further comprising:
obtaining timing information indicating one or more selected reminder times for a bedtime reminder, and
generating the bedtime reminder based on the timing information.

25. The method of claim 15, wherein causing the second set of one or more graphical user interfaces to be displayed further includes:
- obtaining a recommended bedtime based on a calculation accounting for, at least in part, the scheduled waketime and a sleep efficiency based on sleep data associated with one or more users stored in the sleep log data store, and
- causing the recommended bedtime to be displayed in a graphical user interface element of at least one graphical user interface of the second set of one or more graphical user interfaces.

26. The method of claim 12, further comprising:
- causing, based on a determination that the sleep state duration data of the user is not within a threshold amount of the selected sleep duration, one or more of: a second recommended bedtime, a recommended sleep duration, and a recommended waketime to be displayed in a graphical user interface element of at least one graphical user interface of a third set of one or more graphical user interfaces.

27. The method of claim 26, wherein the causing the information associated with the determination of whether the sleep state duration data of the user for one of the sleep sessions of the user is within the threshold amount of the selected sleep duration to be displayed includes:
- causing a timeline to be displayed showing a graphical indication of the threshold amount relative to the timeline and a graphical indication of the sleep state duration data relative to the timeline.

28. The method of claim 1, further comprising:
- determining whether the sleep state duration data of the user for at least one of the one or more sleep sessions of the user is within a threshold amount of the selected sleep duration, and
- causing information associated with the determination of whether the sleep state duration data of the user for one of the sleep sessions of the user is within the threshold amount of the selected sleep duration to be displayed in a graphical user interface element of at least one graphical user interface of a second set of one or more graphical user interfaces.

* * * * *